US010738054B2

(12) United States Patent
Scherz et al.

(10) Patent No.: US 10,738,054 B2
(45) Date of Patent: Aug. 11, 2020

(54) SYNERGISTIC COMPOSITIONS COMPRISING (R)-DIMIRACETAM (1) AND (S)-DIMIRACETAM (2) IN A NON-RACEMIC RATIO

(71) Applicant: Metys Pharmaceuticals AG, Basel (CH)

(72) Inventors: Michael Scherz, Oberwil (CH); Carlo Farina, Milan (IT)

(73) Assignee: METYS PHARMACEUTICALS AG, Basel (CH)

( * ) Notice: Subject to any disclaimer, the term of this patent is extended or adjusted under 35 U.S.C. 154(b) by 0 days.

(21) Appl. No.: 15/992,529

(22) Filed: May 30, 2018

(65) Prior Publication Data

US 2018/0346472 A1 Dec. 6, 2018

(30) Foreign Application Priority Data

May 31, 2017 (EP) .................................... 17173760

(51) Int. Cl.

| C07D 487/04 | (2006.01) |
|---|---|
| A61K 45/06 | (2006.01) |
| A61K 31/4188 | (2006.01) |
| A61K 31/7068 | (2006.01) |
| A61K 31/7072 | (2006.01) |
| A61K 31/708 | (2006.01) |
| A61P 25/02 | (2006.01) |
| A61P 19/02 | (2006.01) |
| A61P 25/24 | (2006.01) |
| A61K 31/282 | (2006.01) |
| A61K 31/407 | (2006.01) |

(52) U.S. Cl.

CPC .......... *C07D 487/04* (2013.01); *A61K 31/282* (2013.01); *A61K 31/407* (2013.01); *A61K 31/4188* (2013.01); *A61K 31/708* (2013.01); *A61K 31/7068* (2013.01); *A61K 31/7072* (2013.01); *A61K 45/06* (2013.01); *A61P 19/02* (2018.01); *A61P 25/02* (2018.01); *A61P 25/24* (2018.01); *C07B 2200/07* (2013.01); *C07B 2200/13* (2013.01)

(58) Field of Classification Search

CPC .. C07D 487/04; A61K 45/06; A61K 31/4188; A61K 31/7068; A61K 31/7072; A61K 31/708; A61K 31/407; C07B 2200/07; C07B 2200/13

See application file for complete search history.

(56) References Cited

U.S. PATENT DOCUMENTS

2010/0125096 A1 5/2010 Farina et al.
2013/0123509 A1 5/2013 Farina et al.

FOREIGN PATENT DOCUMENTS

| AU | 2012201853 | 4/2012 |
|---|---|---|
| EP | 0 335 483 A2 | 10/1989 |
| EP | 2 857 017 B1 | 5/2016 |
| WO | 9309120 | 5/1993 |
| WO | 0032558 | 6/2000 |
| WO | WO 2008073381 A2 * | 6/2008 |
| WO | 2008/125674 A1 | 10/2008 |
| WO | 2009/058261 A1 | 5/2009 |
| WO | 2012/055057 A1 | 5/2012 |
| WO | 2015/010217 A1 | 1/2015 |
| WO | WO 2015010217 A1 * | 1/2015 |

OTHER PUBLICATIONS

Arnold, et al., "Glutamate receptor gene (GRIN2B) associated with reduced anterior cingulate glutamatergic concentration in pediatric obsessive-compulsive disorder," Psychiatry Res., May 15, 2009, 172(2): 136-139.
Attal, et al., "EFNS guidelines on the pharmacological treatment of neuropathic pain: 2010 revision," European Journal of Neurology, 2010, 17: pp. 1113-1123.
Bril, et al., "Evidence-based guideline: Treatment of painful diabetic neuropathy," Report of the American Academy of Neurology, the American Association of Neuromuscular and Electrodiagnostic Medicine, and the American Academy of Physical Medicine and Rehabilitation, May 17, 2011, pp. 1758-1765.
Bullock, et al., "An openlabel study of CP101,606 in subjects with a severe traumatic head injury or spontaneous intracerebral hemorrhage," Ann NY Acad Sci., 1999; 890:518.
Christensen, et al., "The antinociceptive effect of combined systemic administration of morphine and the glycine/NMDA receptor antagonist, (+)-HA966 in a rat model of peripheral neuropathy," British Journal of Pharmacology (1998) 125, pp. 1641-1650.
Cull-Candy, et al., "NMDA receptor subunits: diversity, development and disease," Current Opinion in Neurobiology, Elsevier Science Ltd., 2001, 11: pp. 327-335.
Dalmau, et al., "Anti-NMDA-receptor encephalitis: case series and analysis of the effects of antibodies," Lancet Neurol., Dec. 2008; 7(12): pp. 1091-1098.
Di Cesare Mannelli, et al., "A model of neuropathic pain induced by sorafenib in the rat: Effect of dimiracetam," NeuroToxicology 50, 2015, pp. 101-107.
Di Cesare Mannelli, et al., "Effects of Dimiracetam on oxaliplatin-induced hyperalgesia and allodynia in the rat," Journal of Clinical Oncology, vol. 33, No. 15, Jan. 31, 2017, retrieved via the internet at http://ascopubs.org/doi/abs/10.1200/jco.2015.33.15_suppl.e20650.

(Continued)

*Primary Examiner* — Shirley V Gembeh
(74) *Attorney, Agent, or Firm* — Kilpatrick Townsend & Stockton LLP

(57) ABSTRACT

The present invention relates to a composition of enantiomers of 3,6,7,7a-tetrahydro-1H-pyrrolo[1,5-a]imidazole-2,5-dione and pharmaceutically acceptable solvates or co-crystals thereof in a certain ratio, a pharmaceutical composition comprising said composition, its use as a medicament and the use of the inventive compositions or pharmaceutical compositions in the treatment and/or prevention of a disease or disorder typically and preferably selected from peripheral sensory neuropathy, preferably peripheral neuropathic pain; seizure; depression; or cognitive impairment.

23 Claims, 7 Drawing Sheets

(56) References Cited

OTHER PUBLICATIONS

Dorval, et al., "Association of the glutamate receptor subunit gene GRIN2B with attention-deficit/hyperactivity disorder," Genes Brain Behav., Jul. 2007; 6(5): pp. 444-452.
Dubinsky, et al., "Practice Parameter: Treatment of postherpetic neuralgia: An evidence-based report of the Quality Standards Subcommittee of the American Academy of Neurology," American Academy of Neurology, 2004; 63: pp. 959-965.
Duty, "Targeting Glutamate Receptors to Tackle the Pathogenesis, Clinical Symptoms and Levodopa-Induced Dyskinesia Associated with Parkinson's Disease," CNS Drugs, 2012, 26: pp. 1017-1032.
Fariello, et al., "Antidepressant-like activity of dimiracetam (NT-11624) in the rat forced swimming test," Society for Neuroscience, Nov. 16, 2011, 2 pages.
Fariello, et al., "Broad spectrum and prolonged efficacy of dimiracetam in models of neuropathic pain," Neuropharmacology, vol. 81, 2014, pp. 85-94.
Finnerup, et al., "Neuropathic pain: an updated grading system for research and clinical practice," International Association for the Study of Pain, Pain, Aug. 2016, vol. 157, No. 8, pp. 1599-1606.
Foster, et al., "Taking apart NMDA receptors,", Nature, vol. 329, Oct. 1, 1987, pp. 395-396.
Fuller, et al., "Differential expression of the NMDA NR2B receptor subunit in motoneuron populations susceptible and resistant to amyotrophic lateral sclerosis," Neuroscience Letters, vol. 399, 2006, pp. 157-161.
Grasselli, et al., "Abnormal NMDA receptor function exacerbates experimental autoimmune encephalomyelitis," British Journal of Pharmacology, 2013, 168, pp. 502-517.
Grimwood, et al., "NR2B-containing NMDA receptors are upregulated in temporal cortex in schizophrenia," NeuroReport, vol. 10, No. 3, Feb. 25, 1999, pp. 461-465.
Gronseth, et al., "Practice Parameter: The diagnostic evaluation and treatment of trigeminal neuralgia (an evidence-based review)," Report of the Quality Standards Subcommittee of the American Academy of Neurology and the European Federation of Neurological Societies, Neurology, 2008, 71: pp. 1183-1190.
Guitton, et al., "Blockade of Cochlear NMDA Receptors Prevents Long-Term Tinnitus during a Brief Consolidation Window after Acoustic Trauma," Hindawi Publishing Corporation, Neural Plasticity, vol. 2007, Article ID 80904, 11 pages.
Hackos, et al., "Diverse modes of NMDA receptor positive allosteric modulation: Mechanisms and consequences," Neuropharmacology 112, 2017, pp. 34-45.
Haller, et al., "NR2B subunit-specific NMDA antagonist Ro25-6981 inhibits the expression of conditioned fear: a comparison with the NMDA antagonist MK-801 and fluoxetine," Behavioural Pharmacology, 2011, 22: pp. 113-121.
Hanson, et al., "Altered GluN2B NMDA receptor function and synaptic plasticity during early pathology in the PS2APP mouse model of Alzheimer's disease," Neurobiol Dis., Feb. 2015; 74: pp. 254-262.
Hu, et al., "Expression of immediate-early genes in the dorsal cochlear nucleus in salicylate-induced tinnitus," Eur Arch Otorhinolaryngol, 2016, 273: pp. 325-332.
Jin, et al., "Mechanism of Positive Allosteric Modulators Acting on AMPA Receptors," The Journal of Neuroscience, Sep. 28, 2005, 25(39): pp. 9027-9036.
Karakas, et al., "Crystal structure of a heterotetrameric NMDA receptor ion channel," Science, May 30, 2014, 344(6187): pp. 992-997.
Kowal, et al., "Human lupus autoantibodies against NMDA receptors mediate cognitive impairment," Proceedings of the National Academy of Sciences, vol. 103, No. 52, Dec. 26, 2006, pp. 19854-19859.
Latremoliere, et al., "Central Sensitization: A Generator of Pain Hypersensitivity by Central Neural Plasticity," J Pain, Sep. 2009, 10(9): pp. 895-926.
Leaderbrand, et al., "Co-activation of NR2A and NR2B subunits induces resistance to fear extinction," Neurobiol Learn Mem. Author manuscript; available in PMC, Mar. 18, 2015, 16 pages.
Leaver, et al., "Annual Scientific Meeting of ASCEPT 2007: Neuroprotective Effects of a Selective N-Methyl-d-Aspartate NR2B Receptor Antagonist in the 6-Hydroxydopamine Rat Model of Parkinson's Disease," Clinical and Experimental Pharmacology and Physiology, 2008, 35, pp. 1388-1394.
Lee, et al., "NMDA receptor structures reveal subunit arrangement and pore architecture," Nature, Jul. 10, 2014, 511(7508): pp. 191-197.
Li, et al., "Enhanced Striatal NR2B-Containing N-Methyl-D-Aspartate Receptor-Mediated Synaptic Currents in a Mouse Model of Huntington Disease," J Neurophysiol, 2004, 92: pp. 2738-2746.
Li, et al., "Glutamate NMDA receptor antagonists rapidly reverse behavioral and synaptic deficits caused by chronic stress exposure," Biol Psychiatry, Apr. 15, 2011, 69(8): pp. 754-761.
Li, et al., "Soluble Aβ oligomers inhibit long-term potentiation through a mechanism involving excessive activation of extrasynaptic NR2B-containing NMDA receptors," J Neurosci., May 4, 2011, 31(18): pp. 6627-6638.
Marieb, et al., "Gross Anatomy of the Nervous System: An Overview," excerpt from Human Anatomy, Global Edition, Pearson, 2016, 1 page.
Martucci, et al., "N-methyl-d-aspartate receptor NR2B subunit gene GRIN2B in schizophrenia and bipolar disorder: Polymorphisms and mRNA levels," Schizophrenia Research 84, 2006, pp. 214-221.
Mayer, et al., "Excitatory amino acid receptors, second messengers and regulation of intracellular $Ca^{2+}$ in mammalian neurons," Trends in Pharmacological Sciences, vol. 11, Issue 6, Jun. 1990, pp. 254-260.
Morissette, et al., "Prevention of dyskinesia by an NMDA receptor antagonist in MPTP monkeys: effect on adenosine A2A receptors," Synapse, Sep. 1, 2006, 60(3): 23950.
Moulin, et al., "Consensus Statement: Pharmacological management of chronic neuropathic pain: Revised consensus statement from the Canadian Pain Society," Pain Research & Management, vol. 19, No. 6, Nov./Dec. 2014, pp. 328-335.
Nagy, et al., "The NR2B subtype of NMDA receptor: a potential target for the treatment of alcohol dependence," Current Drug Targets—CNS & Neurological Disorders, Jun. 2004; 3(3): 169-79.
Naskar, et al., "Saving the Nerve from Glaucoma: Memantine to Caspaces," Seminars in Ophthalmology, vol. 14, No. 3, Sep. 1999, pp. 152-158.
Naspolini, et al., "Traxoprodil decreases pentylenetetrazol-induced seizures," Epilepsy Research, 2012, 100, pp. 12-19.
Ogden, et al., "Contribution of the M1 Transmembrane Helix and Pre-M1 Region to Positive Allosteric Modulation and Gating of N-Methyl-D-Aspartate Receptors," Molecular Pharmacology, May 2013, 83: pp. 1045-1056.
Orgogozo, et al., "Efficacy and safety of memantine in patients with mild to moderate vascular dementia: a randomized, placebo-controlled trial (MMM 300)," Stroke, Jul. 2002, 33(7):1834-9, retrieved via the internet at https://www.ncbi.nlm.nih.gov/pubmed/12105362.
Paoletti, et al., "NMDA receptor subunit diversity: impact on receptor properties, synaptic plasticity and disease," Nature Reviews, Neuroscience, vol. 14, Jun. 2013, pp. 383-400.
Peeters, et al., "Effects of Pan- and Subtype-Selective N-Methyl-$_D$-aspartate Receptor Antagonists on Cortical Spreading Depression in the Rat: Therapeutic Potential for Migraine," The Journal of Pharmacology and Experimental Therapeutics, vol. 321, No. 2, Jan. 24, 2007, pp. 564-572.
Pinza, et al., "Synthesis and Pharmacological Activity of a Series of Dihydro-1H-pyrrolo[1,2-a]imidazole-2,5(3H,6H)-diones, a Novel Class of Potent Cognition Enhancers," American Chemical Society, Journal of Medicinal Chemistry, vol. 36, No. 26, May 28, 1993, pp. 4214-4220.
Preskorn, et al., "An Innovative Design to Establish Proof of Concept of the Antidepressant Effects of the NR2B Subunit Selective N-Methyl-$_D$-Aspartate Antagonist, CP-101,606, in Patients With Treatment-Refractory Major Depressive Disorder," Journal of Clinical Psychopharmacology, vol. 28, No. 6, Dec. 2008, pp. 631-637.

(56) References Cited

OTHER PUBLICATIONS

Shen, et al., "Heroin relapse requires long-term potentiation-like plasticity mediated by NMDA2b-containing receptors," Proceedings of the National Academy of Sciences, vol. 108, No. 48, Nov. 29, 2011, pp. 19407-19412.

Smith, et al., "Health and Quality of Life Associated With Chronic Pain of Predominantly Neuropathic Origin in the Community," Clinical Journal of Pain, vol. 23, No. 2, Feb. 2007, pp. 143-149.

Starck, et al., "Drug therapy for acquired pendular nystagmus in multiple sclerosis," Journal of Neurology, Jan. 1997, 244(1):9-16.

Steece-Collier, et al., "Antiparkinsonian Actions of CP-101,606, an Antagonist of NR2B Subunit-Containing N-Methyl-$_D$-Aspartate Receptors," Experimental Neurology, vol. 163, 2000, pp. 239-243.

Straube, "Pharmacology of vertigo/nystagmus/oscillopsia," Current Opinion in Neurology, vol. 18, 2005, pp. 11-14.

Sun, et al., "Mechanism of glutamate receptor desensitization," Nature, vol. 417, May 16, 2002, pp. 245-253.

Tang, et al., "Disturbed $Ca^{2+}$ signaling and apoptosis of medium spiny neurons in Huntington's disease," Proceedings of the National Academy of Sciences, vol. 102, No. 7, Feb. 15, 2005, pp. 2602-2607.

Tang, et al., "Genetic enhancement of learning and memory in mice," Nature, vol. 401, Sep. 2, 1999, pp. 63-69.

Torchio, et al., "Determination of the polar drug dimiracetam in human plasma and serum by column-switching high-performance liquid chromatography," Journal of Chromatography B, vol. 666, 1995, pp. 169-177.

Van Hecke, et al., "Neuropathic pain in the general population: A systematic review of epidemiological studies," Pain, vol. 155, 2014, pp. 654-662.

Wang, et al., "Targeting the NMDA receptor subunit NR2B for treating or preventing age-related memory decline," Expert Opinion on Therapeutic Targets, 2014, 18:10, pp. 1121-1130.

Weickert, et al., "Molecular evidence of N-methyl-$_D$-aspartate receptor hypofunction in schizophrenia," Molecular Psychiatry, 2013, vol. 18, pp. 1185-1192.

Won, et al., "Autistic-like social behaviour in Shank2-mutant mice improved by restoring NMDA receptor function," Nature, vol. 486, Jun. 14, 2012, pp. 261-265.

Wu, et al., "Targeting the NMDA Receptor Subunit NR2B for the Treatment of Neuropathic Pain," Neurotherapeutics: The Journal of the American Society for Experimental NeuroTherapeutics, Oct. 2009, vol. 6, pp. 693-702.

Yang, et al., "Reduced brain infarct volume and improved neurological outcome by inhibition of the NR2B subunit of NMDA receptors by using CP101,606-27 alone and in combination with rt-PA in a thromboembolic stroke model in rats," Journal of Neurosurgery, 2003, vol. 98, pp. 397-403.

Yuan, et al., "Context-Dependent GluN2B-Selective Inhibitors of NMDA Receptor Function are Neuroprotective with Minimal Side Effects," Neuron, Mar. 18, 2015, 85(6): pp. 1305-1318.

Zilliox, "Neuropathic Pain," Continuum Journal, Apr. 2017, vol. 23, No. 2, pp. 512-532.

Camilleri et al., "Chiral high-performance liquid chromatography of some related bicyclic lactams", Journal of Chromatography A, vol. 654, 1993, pp. 207=213.

EP17173760.4, "Extended European Search Report" dated Nov. 22, 2017, 8 Pages.

PCT/EP2018/064125, "International Search Report and Written Opinion" dated Sep. 7, 2018, 12 Pages.

* cited by examiner

SYNERGISTIC COMPOSITIONS COMPRISING (R)-DIMIRACETAM (1) AND (S)-DIMIRACETAM (2) IN A NON-RACEMIC RATIO

CROSS-REFERENCE TO RELATED APPLICATION

This application claims the benefit of priority to European Patent Application No. 17173760.4, filed May 31, 2017, which is incorporated herein by reference in its entirety.

FIELD

The present invention relates to compositions and kits comprising (R)-3,6,7,7a-tetrahydro-1H-pyrrolo[1,5-a]imidazole-2,5-dione ((R)-dimiracetam (1)) and (S)-3,6,7,7a-tetrahydro-1H-pyrrolo[1,5-a]imidazole-2,5-dione ((S)-dimiracetam (2)) in a certain range of ratios and pharmaceutically acceptable solvates or co-crystals thereof, pharmaceutical compositions comprising said compositions, their use as a medicament and the uses of the inventive compositions or pharmaceutical compositions or kits for the treatment and/or prevention of a disease or disorder typically and preferably selected from peripheral sensory neuropathy, preferably peripheral neuropathic pain and other symptoms of peripheral sensory neuropathy; and neuropsychiatric conditions, such as seizure; depression; or cognitive impairment; and motoneuron diseases, such as amyotrophic lateral sclerosis.

BACKGROUND

Glutamic acid is an excitatory neurotransmitter that is widely present in the brain. The first indication of its role as an excitatory messenger emerged in the 1950's, when it was observed that intravenous administration of glutamate induces convulsions. However, the detection of the entire glutamatergic neurotransmitter system, with biosynthetic and catabolic enzymes, cellular uptake mechanisms, intracellular storage and release systems, and its cell-surface ion channels and G protein-coupled receptors, did not take place until the 1970's and 1980's, when suitable pharmacological tools were first identified. It was in the 1990's that the newly emergent tools of molecular biology provided means for the molecular identification and classification of glutamatergic ion channels, receptors, transporters, etc.

The membrane-bound ion channels that are gated by the excitatory amino acids glutamate and glycine, and that also respond to the xenobiotic compound N-methyl-D-aspartate (NMDA), control the flow of both divalent and monovalent cations into pre- and post-synaptic neural cells (see Foster et al., Nature 1987, 329:395-396; Mayer et al., Trends in Pharmacol. Sci. 1990, 11:254-260). They are molecularly, electrophysiologically, and pharmacologically distinct from the glutamate-gated, cation-conducting ion channels that respond to the xenobiotic agents kainate or alpha-amino-3-hydroxy-5-methyl-4-isoxazolepropionic acid (AMPA); and they are similarly distinct from the family of glutamate-gated G protein-coupled receptors, the so-called metabotropic glutamate receptors.

The NMDA-preferring glutamate-gated ion channel has a hetero-tetrameric structural basis: two obligatory GluN1 units and two variable GluN2 receptor subunits encoded by the GRIN1 gene and one of four GRIN2 genes, respectively. One or both GluN2 subunits can be potentially replaced by a GluN3A or a GluN3B subunit. The GRIN1 gene product has 8 splice variants while there are 4 different GRIN2 genes (GRIN2A-D) encoding four distinct GluN2 subunits. The glycine binding site is present on the GluN1 subunit and the glutamate binding site is present on the GluN2 subunit (Paoletti P et al., Nat Rev Neurosci. 2013; 14(6):383-400).

Multiple classes of positive or negative allosteric modulators of glutamate-gated ion channels have been described; they bind glutamate-gated ion channels at the inter-subunit interface of the ligand-binding domains (LBD's) of the respective ion channels, a site that is distinct from the glutamate- or the glycine-binding sites present within the LBD (Sun et al., 2002; Jin et al., 2005; Hackos et al., 2016). Allosteric modulators have also been described (Wang et al. 2017) that bind to the trans-membrane domain of the NMDA-type glutamate-gated ion channel, where a highly-conserved structural motif (the so-called "Lurcher domain") restricts ionic flow through the pore when the ion channel is in the closed or deactivated state (Karakas and Furukawa, 2014; Lee et al., 2014; Ogden and Traynelis, 2013).

Allosteric modulators of glutamate-gated ion channels have therapeutic potential, and even utility in healthy individuals, in diverse fields, such as learning, memory processing, mood, attention, emotion, motoneuron disease, peripheral sensory neuropathy and pain perception (Cull-Candy S et al., Curr Opin Neurobiol. 2001; 11(3):327-35).

Compounds that modulate NMDA receptor function can be useful in treatment of many neurological and psychiatric disorders including but not limited to bipolar disorder (Martucci L et al., Schizophrenia Res, 2006; 84(2-3):214-21), major depressive disorder (Li N et al., Biol Psychiatry. 2011; 69(8):754-61), treatment-resistant depression (Preskorn S H et al. J Clin Psychopharmacol. 2008; 28(6):631-7) and other mood disorders (including schizophrenia (Grimwood S et al., Neuroreport. 1999; 10(3):461-5), ante- and postpartum depression (Weickert C S et al. Molecular Psychiatry (2013) 18, 1185-1192), seasonal affective disorder, and the like; Alzheimer's disease (Hanson J E et al., Neurobiol Dis. 2015; 74:254-62; Li S et al., J Neurosci. 2011; 31(18):6627-38) and other dementias (Orgogozo J M et al. Stroke 2002, 33: 1834-1839), Parkinson's disease (Duty S, CNS Drugs. 2012; 26(12):1017-32; Steece-Collier K et al., Exp Neurol. 2000; 163(1):239-43; Leaver K R et al. Clin Exp Pharmacol-Physiol. 2008; 35(11):1388-94), Huntington's chorea (Tang T S et al., Proc Natl Acad Sci USA. 2005; 102(7):2602-7; Li L et al., J Neurophysiol. 2004; 92(5):2738-46), multiple sclerosis (Grasselli G et al., Br J Pharmacol. 2013; 168(2): 502-17), cognitive impairment (Wang D et al. 2014, Expert Opin Ther Targets 2014; 18(10):1121-30), head injury (Bullock M R et al., Ann NY Acad Sci. 1999; 890:51-8), spinal cord injury, stroke (Yang Y et al., J Neurosurg. 2003; 98(2):397-403), epilepsy (Naspolini A P et al., Epilepsy Res. 2012 June; 100(1-2):12-9), movement disorders (e.g. dyskinesias) (Morissette M et al., Mov Disord. 2006; 21(1):9-17), various neurodegenerative diseases (e.g. amyotrophic lateral sclerosis (Fuller P I et al., Neurosci Lett. 2006; 399(1-2):157-61) or neurodegeneration associated with bacterial or chronic infections, glaucoma (Naskar R et al. Semin Ophthalmol. 1999 September; 14(3):152-8), pain (e.g. chronic, cancer, post-operative and neuropathic pain (Wu L J and Zhuo M, Neurotherapeutics. 2009; 6(4):693-702), diabetic neuropathy, migraine (Peeters M et al., J Pharmacol Exp Ther. 2007; 321(2):564-72), cerebral ischemia (Yuan H et al., Neuron. 2015; 85(6):1305-18), encephalitis (Dalmau J. et al., Lancet Neurol. 2008; 7(12):1091-8.), autism and autism spectrum disorders (Won H. et al., Nature. 2012; 486(7402):261-5), memory and learning disorders (Tang, Y. P. et al., Nature. 1999; 401(6748):63-9), obsessive compulsive disorder (Arnold P D et al., *Psychiatry Res.* 2009; 172(2):136-9.), attention deficit hyperactivity disorder (ADHD) (Dorval K M et al., *Genes Brain Behav.* 2007; 6(5):444-52), PTSD (Haller J et al. *Behav Pharmacol.* 2011; 22(2):113-21; Leaderbrand K et al. *Neurobiol Learn Mem.* 2014; 113:35-40), tinnitus (Guitton M J, and Dudai Y, NeuralPlast.2007; 80904; Hu S S et al. 2016; 273(2): 325-332), sleep disorders (like narcolepsy or excessive daytime sleepiness, patent WO 2009/058261 A1), vertigo and nystagmus (Straube A. et al., *Curr Opin Neurol.* 2005; 18(1):11-4; Starck M et al. *J Neurol.* 1997 January; 244(1): 9-16), anxiety, autoimmunological disorders like neuropsychiatric systemic lupus erythematosus (Kowal C et al. *Proc. Natl. Acad. Sci. U.S.A.* 2006; 103, 19854-19859) and addictive illnesses (e.g. alcohol addiction, drug addiction) (Nagy J, 2004, *Curr Drug Targets CNS Neurol Disord.* 2004; 3(3):169-79.; Shen H et al., *Proc Natl Acad Sci USA.* 2011; 108(48):19407-12).

The symptoms of peripheral sensory neuropathy, including one of the most prominent symptoms, peripheral neuropathic pain (Zilliox L A, 2017), are frequently encountered clinical conditions: the prevalence in the general population has been estimated to be between 7% and 10% (van Hecke O et al., 2014). In the United States, painful diabetic peripheral neuropathy alone is estimated to affect approximately 10 million people. Peripheral sensory neuropathy is often resistant to treatment and is associated with poor patient satisfaction of their treatment. Several medications have been shown to be effective in treating peripheral sensory neuropathy associated with diabetic neuropathy and post-herpetic neuralgia, and these medications are often used to treat neuropathic pain associated with other conditions as well. These treatments often have unwanted adverse effects and discontinuation of treatment may be problematic. It is important to recognize that peripheral sensory neuropathy affects many aspects of daily life and is associated with poor general health, reduction in quality of life, poor sleep, and higher anxiety and depression. In fact, measures of quality of life in people with chronic peripheral sensory neuropathy were rated as low as for patients with clinical depression, coronary artery disease, recent myocardial infraction, or poorly controlled diabetes mellitus (Smith B H et al., 2007).

The American Academy of Neurology has published practice guidelines on the treatment of painful diabetic neuropathy (Bril V et al., 2011), post-herpetic neuralgia (Dubinsky R M et al., 2004), and trigeminal neuralgia (Gronseth G et al., 2008). Several other clinical practice guidelines for the treatment of neuropathic pain also have been published (Attal N et al., 2010; Moulin D, et al., 2014).

Sensory neuropathy is commonly classified as central or peripheral, depending on the site of the lesion that is causing the symptoms. Examples of conditions associated with peripheral sensory neuropathy are diabetic neuropathy, human immunodeficiency virus-associated neuropathy, chemotherapy-induced peripheral neuropathy, post-herpetic neuralgia, trigeminal neuralgia, complex regional pain syndrome, compressive mononeuropathies, radiculoneuropathies, inflammatory neuropathies (acute and chronic inflammatory demyelinating polyneuropathy), post-traumatic neuropathy, or phantom limb neuropathy.

Typically, peripheral sensory neuropathy has both positive and negative symptoms. Positive symptoms include tingling ("pins and needles"), prickling, lightening-like or lancinating sensations, aching, knife-like, pulling or tightening-like symptoms, burning- or searing-like, or electrical pain. Negative symptoms include numbness, deadness, or the feeling of wearing socks. Some unique aspects of peripheral sensory neuropathy include hyperalgesia (an increased response to a stimulation is normally painful); allodynia (pain due to a stimulus that typically does not provoke pain); hyperesthesia (an increased sensitivity to stimulation); paresthesia (abnormal sensation, whether provoked or spontaneous); dysesthesia (unpleasant abnormal sensation); hypoesthesia (diminished pain in response to a normally painful stimulus); analgesia (loss of pain sensation); and anaesthesia (loss of sensation). The positive signs or symptoms are thought to represent excessive activity in a sensory pathway due to a lowered threshold or heightened excitability. Negative signs and symptoms are experienced as diminished or absent feeling and are due to a loss of sensory function.

While some pharmacological agents have been found to be effective in the treatment of symptoms of peripheral sensory neuropathy (Finnerup N B et al., 2015), only a minority of patients suffering from neuropathic pain show a complete response to drug therapy. For the majority of patients, it is reasonable to expect that treatment will make the pain tolerable. In general, a 30% reduction of a pain on an 11-point numerical rating scale is considered clinically important and constitutes "moderate relief" or "much improved." It is also important to recognize and treat comorbidities, such as anxiety and depression, and secondary treatment goals may include improving sleep, advancing function, and enhancing overall quality of life. These goals are best achieved when pharmacologic therapy is one component of a multi-disciplinary approach to treatment.

Neuropathic pain medications approved by the US Food and Drug Administration are carbamazepine, duloxetine, pregabalin, gabapentin, topical lidocaine, and topical capsaicin. Tramadol and opioid analgesics are effective in different types of neuropathic pain but are generally not recommended as first-line treatments because of concerns about long-term safety. However, they are recommended as first-line treatments in acute neuropathic pain, neuropathic pain due to cancer, and episodic exacerbations of severe neuropathic pain. The use of strong opioids (codeine, morphine, oxycodone and fentanyl) in the treatment of a variety of neuropathic pain conditions is controversial and a public health concern given the rising number of deaths related to prescription opioids. The serious risks of overdose, dependence, and addiction which these drugs carry may outweigh the potential benefits.

Thus, there remains an urgent and important medical need for the development of novel, orally-effective therapies for peripheral sensory neuropathy and peripheral neuropathic pain that are toxicologically benign and devoid of the potential for dependence and addiction phenomena.

There also remains an important medical need for the development of novel, orally-effective therapies for neuropsychiatric diseases, such as those described in the 5$^{th}$ version of the Diagnostic and Statistical Manual of Mental Disorders (DSM-5); and for the treatment of motoneuron diseases, such as amyotrophic lateral sclerosis.

Dimiracetam (2,5-dioxohexahydro-1H-pyrrolo[1,2-a] imidazole—IUPAC name: (RS)-3,6,7,7a-tetrahydro-1H-pyrrolo[1,5-a]imidazole-2,5-dione) is a bicyclic 2-pyrrolidinone derivative and a nootropic member of the racetam family:

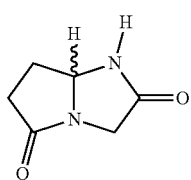

AU 2012/201853 discloses the use of dimiracetam, or a pharmaceutically acceptable solvate thereof, alone or in association with other active principles, in the manufacture of a medicament useful for the treatment and/or prevention of chronic pain.

WO 93/09120 relates to certain processes for preparing certain fused imidazole derivatives and in particular for preparing chiral fused imidazole derivatives.

U.S. Pat. No. 5,200,406 mentions that dimiracetam may be useful in restoring learning and treating memory difficulties. One example of a disease to be treated with dimiracetam is Alzheimer's disease.

Dimiracetam was originally developed as a cognition enhancer and has been shown to be able to improve learning and memory in rats (Pinza M et al., 1993; EP 3 354 83). In single-dose healthy human volunteer studies (Torchio L et al., 1995), dimiracetam was found to ameliorate, versus placebo, certain measures of the transient decline in cognitive performance induced by injection of scopolamine. Further medical uses of dimiracetam have been described including in particular its broad efficacy in rodent models of neuropathic pain. The efficacy of dimiracetam in the treatment of neuropathic pain of different origin has been documented in established models of neuropathic pain induced by nerve injury, chemotherapy, or mono-iodoacetate (MIA)-induced osteoarthritis (Fariello R et al., 2014); Di Cesare Mannelli L et al., 2015a; Di Cesare Mannelli L et al., 2015b; WO 2008/125674; EP 2 857 017 B1, US 2010/0125096; WO 2012/055057). The chemotherapy-induced symptoms of neurotoxicity are responsive to dimiracetam, regardless of which chemotherapeutic agent is used: dideoxycytidine- (ddC-), oxaliplatin-, vincristine-, paclitaxel-, and sorafenib-derived models all respond to the effects of dimiracetam; and dimiracetam has been shown to be effective not only in treating, but also in preventing the symptoms brought on by administration of these chemotherapeutic agents. A single oral administration of dimiracetam can completely, but transiently, revert hyperalgesia and allodynia back to the level of healthy controls. With repeated twice-daily oral administration, the maximal effect becomes sustained, without evidence of tachyphylaxis, or tolerance, despite dose diminution and increased inter-dose interval to once-daily oral administration. Furthermore, the effects of dimiracetam are disease-specific: in a unilateral chronic constriction injury (CCI) model, where rats develop a state of peripheral neuropathic pain in one hind-limb subjected to surgical placement of a ligature around the sciatic nerve, but not in the other limb subjected to sham surgery, a single oral dose of dimiracetam reduced the pain response only in the nerve-ligated limb, without affecting algesia or allodynia in the sham-operated limb; this profile is markedly distinct from effects of, for example, opiates, which affect both limbs in this model (Christensen D et al., 1998).

The mechanism of dimiracetam's pharmacological actions have been explored using synaptosomal preparations of the hippocampus and the spinal cord. This assay is intended to pharmacologically mimic the physiological process of glutamate-triggered glutamate release; its pH-, $Zn^{2+}$- and ifenprodil-sensitivities suggest involvement of an NMDA-receptor isoform containing pH-sensitive GluN1 and GluN2A subunits (Fariello et al., 2014). Inhibition of glutamate signaling is an established basis for the prevention or the treatment of neuropathic pain (Latremoliere and Woolf, 2009). In the spinal cord, at the junction where peripheral sensory afferents make their first and only synaptic connection to the interneurons of the central nervous system (Marieb, Wilhelm and Mallat, 2017), glutamate-induced glutamate release is a component of the up-regulated, or "sensitized" signaling which results from a damaged peripheral nerve (Latremolier and Woolf, 2009).

In synaptosomal preparations of the hippocampus, dimiracetam is a moderately potent inhibitor with an $IC_{50}$ of approximately 3 µM for inhibiting NMDA-plus-glycine-triggered release of [$^3$H]-D-aspartate previously loaded into the synaptosomal preparation. In synaptosomal preparations of the spinal cord, however, dimiracetam is much more potent, with an $IC_{50}$ of approximately 20 nM for inhibiting the NMDA-plus-glycine-triggered [$^3$H]-D-aspartate release (Fariello R et al., 2014).

Dimiracetam's ability to block glutamate-triggered glutamate release in the spinal cord underlies its utility in the prevention or treatment of peripheral sensory neuropathies; other mechanisms in the brain may underlie its efficacy in the treatment of depression in rats (Fariello et al., 2011; WO 2015/010217); and its efficacy in rat and human models of scopolamine-induced cognitive impairment (Pinza et al., 1993).

Dimiracetam is a chiral compound with a single stereocenter, but it has undergone clinical development as a racemic mixture of its (R)- and (S)-enantiomers. This was done even though (R)-dimiracetam is the more active enantiomer (WO 2008/125674), because the racemate of dimiracetam has been found to be even more potent than either of the single enantiomers. For example, in rats pretreated with 2',3'-dideoxycytidine (ddC, zalcitabine), a single oral dose of (R)-dimiracetam resulted in partial efficacy response, while the (S)-enantiomer resulted in a smaller response than the corresponding dose of the (R)-enantiomer. On the other hand, racemic dimiracetam gave a superior response compared to either (R)- or (S)-dimiracetam alone (WO 2008/125674). This rank order of potency of (S)-, (R)-, and racemic dimiracetam is also seen in the effect of dimiracetam on reverting MIA-induced hyperalgesia (WO 2008/125674).

SUMMARY

It has now been surprisingly and unexpectedly found that compositions of (R)- and (S)-enantiomers of dimiracetam having an enantiomeric excess (ee) of the (R)-dimiracetam (1) greater than or equal to 30% and lower than or equal to 60% exhibit greater pharmacological potency than the corresponding individual enantiomers or even than the racemate and thus provide a synergistic effect that could not have been predicted based on the potency of the individual enantiomers or the racemate. These compositions preferably inhibit NMDA plus glycine-evoked [$^3$H]-D-aspartic acid release from rat spinal synaptosomes by at least about 40%, preferably at least about 45%, at a concentration of about 10 nM.

Thus, it has been surprisingly and unexpectedly found that the preferred inventive composition with an enantiomeric excess of (R)-dimiracetam of 33% (corresponding to a 2:1 (R):(S) ratio of the dimiracetam enantiomers) inhibits NMDA plus glycine-evoked [$^3$H]-D-aspartic acid release from rat spinal synaptosomes by about 50% at a concentration of 10 nM (FIG. 1A, Table 1). The further preferred inventive composition with an enantiomeric excess of (R)-dimiracetam of 50% (corresponding to a 3:1 (R):(S) ratio of the dimiracetam enantiomers) even inhibits NMDA plus glycine-evoked [$^3$H]-D-aspartic acid release from rat spinal synaptosomes by 52% at a concentration of 1 nM (FIG. 1B, Table 1). In comparison, racemic dimiracetam inhibits NMDA plus glycine-evoked [$^3$H]-D-aspartic acid release from rat spinal synaptosomes by 36% at a concentration of 10 nM, corresponding to an estimated $IC_{50}$ of 15 nM (FIG. 1C; Table 1); (R)-dimiracetam has an estimated $IC_{50}$ of 123 nM (FIG. 1D); and (S)-dimiracetam has an estimated $IC_{50}$ of 418 nM (FIG. 1E).

These surprising results are confirmed in further different rat models of peripheral neuropathic pain, such as the MIA-induced knee arthritis model or the oxaliplatin-induced model of neuropathic pain. Thus, the inventive compositions with an enantiomeric excess of (R)-dimiracetam are much more efficient than the racemic mixture of dimiracetam in reducing peripheral neuropathic pain in the paw-pressure test after administration of sodium monoiodoacetate (MIA; FIG. 2), or in the prevention of oxaliplatin-induced peripheral neuropathic pain (FIG. 3). The inventive compositions with an enantiomeric excess of (R)-dimiracetam are also much more efficient than compositions in which an excess of the (S)-enantiomer of dimiracetam is present (FIG. 2).

Therefore, the inventive compositions of (R)- and (S)-enantiomers of dimiracetam having an enantiomeric excess (ee) of (R)-dimiracetam higher than or equal to 30% and lower than or equal to 60% are pharmacologically more effective at a given dose, as compared to either the pure enantiomers alone or to racemic dimiracetam. The term racemic dimiracetam refers to a 1:1 by weight mixture of (R)- and (S)-enantiomers, which thus has an enantiomeric excess (ee) of (R)-dimiracetam of 0%. Thus, the effect associated with the present invention is a synergistic effect that surprisingly results from a specific range of ratios between (R)-dimiracetam and (S)-dimiracetam.

Since rat plasma concentration-time profiles after oral administration of either (R)- or (S)-dimiracetam are identical, and the (R)- and (S)-enantiomers do not to interconvert in vivo (FIG. 4A and FIG. 4B, respectively), the behavior of the inventive compositions of enantiomers is not explained by pharmacokinetics or metabolism of the enantiomers. The fact that the (R)- and (S)-enantiomers are both individually effective (albeit with different potency), and that when combined in an appropriate ratio their pharmacological potency is greater than that of the racemate, shows that they share with racemic dimiracetam the same pharmacological mechanism and suitability for the treatment of the same medical indications. Therefore, the inventive compositions are beneficial and can be used for the treatment and/or prevention of a large number of diseases and disorders as set out in the detailed description. The diseases or disorders are typically and preferably selected from peripheral sensory neuropathy, preferably peripheral neuropathic pain and other symptoms of peripheral sensory neuropathy; and neuropsychiatric conditions, such as seizure; depression; or cognitive impairment; and motoneuron diseases, such as amyotrophic lateral sclerosis. More preferably, the disease or disorder is typically selected from peripheral sensory neuropathy, preferably peripheral neuropathic pain; seizure; depression; or cognitive impairment.

In a first aspect, the invention provides for a composition comprising (R)-3,6,7,7a-tetrahydro-1H-pyrrolo[1,5-a]imidazole-2,5-dione ((R)-dimiracetam (1)) and (S)-3,6,7,7a-tetrahydro-1H-pyrrolo[1,5-a]imidazole-2,5-dione ((S)-dimiracetam (2)),

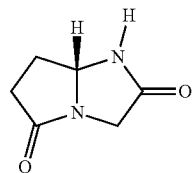

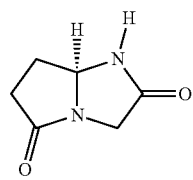

and/or pharmaceutically acceptable solvates or co-crystals thereof, wherein the enantiomeric excess (ee) of said (R)-dimiracetam (1) is equal to or higher than 30% and lower than or equal to 60%.

One specific example of such a composition according to the present invention is a non-racemic mixture of 3,6,7,7a-tetrahydro-1H-pyrrolo[1,5-a]imidazole-2,5-dione (dimiracetam) and pharmaceutically acceptable solvates or co-crystals thereof, wherein said non-racemic mixture comprises (R)-3,6,7,7a-tetrahydro-1H-pyrrolo[1,5-a]imidazole-2,5-dione ((R)-dimiracetam (1)) and (S)-3,6,7,7a-tetrahydro-1H-pyrrolo[1,5-a]imidazole-2,5-dione ((S)-dimiracetam (2)) in an enantiomeric excess (ee) of said (R)-dimiracetam (1) of higher than or equal to 30% and lower than or equal to 60%.

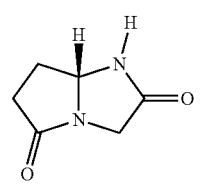

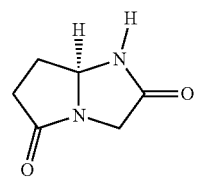

In a further aspect, the invention provides for a pharmaceutical composition comprising the composition of the present invention, e.g. the non-racemic mixture of the invention, and a pharmaceutically acceptable carrier.

In again a further aspect, the invention provides for a kit of parts comprising (R)-dimiracetam (1) and (S)-dimiracetam (2) and instructions for combining (R)-dimiracetam (1) and (S)-dimiracetam (2) to obtain an enantiomeric excess (ee) of said (R)-dimiracetam (1) of equal to or higher than 30% and lower than or equal to 60%. In this aspect, the same preferred ranges of the enantiomeric excess (ee) of said (R)-dimiracetam (1) and enantiomeric ratios of (R)-dimiracetam (1) to (S)-dimiracetam (2) as set out herein with respect to the composition apply.

In again a further aspect, the invention provides for the composition of the invention or the pharmaceutical composition of the invention or the kit of the invention for use as a medicament.

In again a further aspect, the invention provides for the composition of the invention or the pharmaceutical composition of the invention or the kit of the invention for use in the treatment or prevention of a disease or disorder, wherein the disease or disorder is typically and preferably selected from peripheral sensory neuropathy, preferably peripheral neuropathic pain and other symptoms of peripheral sensory neuropathy; and neuropsychiatric conditions, such as seizure; depression; or cognitive impairment; and motoneuron diseases, such as amyotrophic lateral sclerosis.

In again a further aspect, the invention provides for a method for the treatment and/or prevention of a disease or disorder of an animal, preferably of a human, wherein the disease or disorder is typically and preferably selected from peripheral sensory neuropathy, preferably peripheral neuropathic pain and other symptoms of peripheral sensory neuropathy; and neuropsychiatric conditions, such as seizure; depression; or cognitive impairment; and motoneuron diseases, such as amyotrophic lateral sclerosis, wherein said method comprises administration of the composition of the invention or the pharmaceutical composition of the invention or the kit of the invention to an animal, preferably to a human.

In again a further aspect, the invention provides for the use of the composition of the invention or the pharmaceutical composition of the invention or the kit of the invention in the manufacture of a medicament for the treatment and/or prevention of a disease or disorder, wherein the disease or disorder is typically and preferably selected from peripheral sensory neuropathy, preferably peripheral neuropathic pain and other symptoms of peripheral sensory neuropathy; and neuropsychiatric conditions, such as seizure, depression, or cognitive impairment; and motoneuron diseases, such as amyotrophic lateral sclerosis.

In again a further aspect, the invention provides for an article of manufacture comprising the composition of the invention or the pharmaceutical composition of the invention, a container or package and a written description and administration instruction such as a package insert.

It is to be understood that the composition of the present application encompasses the non-racemic mixture of the present invention, so that any reference to the composition of the present invention is also to be understood as a reference to the non-racemic mixture of the present invention.

Further aspects and embodiments of the present invention will be become apparent as this description continues.

DESCRIPTION OF FIGURES

In FIG. 1A-E, results are expressed as % increase of basal release, and data are means±S.E.M. of 6 experiments that were run in triplicate.

FIGS. 4A and 4B demonstrate that the in vivo pharmacological superiority of the inventive compositions is not attributable to pharmacokinetic differences.

DETAILED DESCRIPTION

Figure 1A:
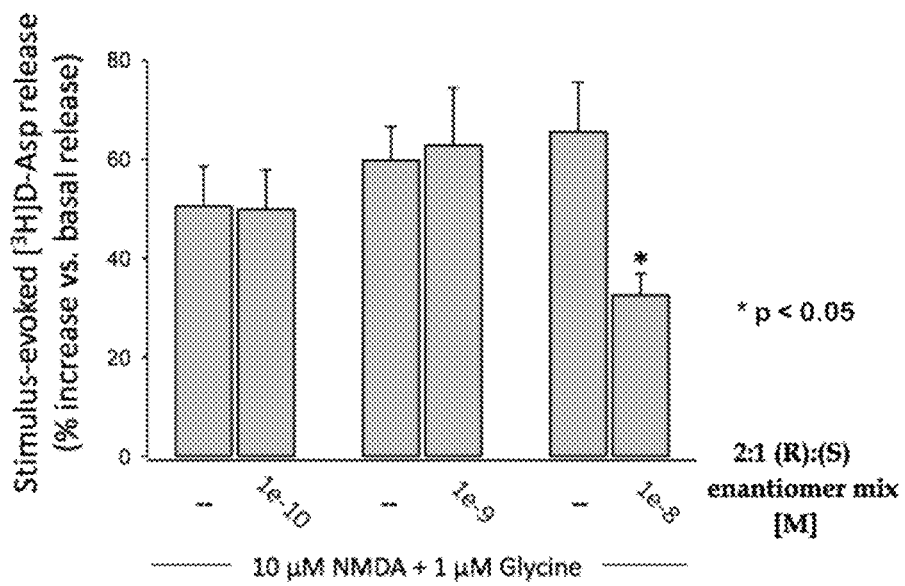
FIG. 1A: Effects of increasing molar concentrations of the inventive composition with an enantiomeric excess of (R)-dimiracetam of 33.3% (corresponding to a 2:1 (R):(S) ratio of the enantiomers) on NMDA (10 μM) plus glycine- (1 μM) stimulated release of [$^3$H]-D-Asp from pre-loaded spinal cord synaptosomes.

Unless defined otherwise, all technical and scientific terms used herein have the same meanings as commonly understood by one of ordinary skill in the art to which this invention belongs.

The term "about" where used to characterize an enantiomeric excess means±4% referring to the given numeric value, if not indicated otherwise. In each of the invention embodiments, "about" can be deleted.

The term "preferably" is used to describe features or embodiments which are not required in the present invention but may lead to improved technical effects and are thus desirable but not essential.

With respect to the numerical values mentioned herein, unless explicitly stated otherwise, the last decimal place of a numerical value preferably indicates its degree of accuracy. Thus, unless other error margins are given, the maximum margin is preferably ascertained by applying the rounding-off convention to the last decimal place. Thus, a value of 2.5 preferably has an error margin of 2.45 to 2.54.

The present invention relates to compositions comprising (R)-3,6,7,7a-tetrahydro-1H-pyrrolo[1,5-a]imidazole-2,5-dione ((R)-dimiracetam (1)) and (S)-3,6,7,7a-tetrahydro-1H-pyrrolo[1,5-a]imidazole-2,5-dione ((S)-dimiracetam (2)) in a certain ratio. It is to be understood that the term "composition" does not require that the (R)-dimiracetam (1) and (S)-dimiracetam (2) have to be mixed. They can be formulated jointly or separately and be administered simultaneously or subsequently, provided that the ratio of (R)-dimiracetam (1) and (S)-dimiracetam (2) achieved in the subject to be treated is as required by the present invention. Preferably, the inventive composition is a mixture of (R)-dimiracetam (1) and (S)-dimiracetam (2), but the inventive composition may also encompass a combination of one or more articles containing (R)-dimiracetam (1) and one or more articles containing (S)-dimiracetam (2), or a combination of one or more articles containing (R)-dimiracetam (1) and one or more articles containing dimiracetam racemate.

Furthermore, the dimiracetam contained in the composition of the present invention has to be present in the overall range of ratios of (R)-dimiracetam (1) and (S)-dimiracetam (2), alternatively expressed as the enantiomeric excess of (R)-dimiracetam (1), required in the present invention. In other words, it is against the gist of the present invention to theoretically split a composition containing equal amounts of (R)-dimiracetam (1) and (S)-dimiracetam (2) into a component containing an excess of (R)-dimiracetam (1) and another component containing an excess of (S)-dimiracetam (2). Thus, in whichever physical form the composition of the present invention is, the composition as a whole has to fulfill the requirements regarding the range of ratios of (R)-dimiracetam (1) and (S)-dimiracetam (2), alternatively expressed as the enantiomeric excess of (R)-dimiracetam (1), of the present invention. It is to be understood that the ratios of (R)-dimiracetam (1) and (S)-dimiracetam (2), alternatively expressed as the enantiomeric excess of (R)-dimiracetam (1), are based on a statistically meaningful number of dimiracetam molecules, which typically exceeds 1000 dimiracetam molecules. In the present invention, the relative amounts of (R)-dimiracetam (1) and (S)-dimiracetam (2) are expressed either in terms of the ratio of (R)-dimiracetam (1) and (S)-dimiracetam (2) or in terms of the enantiomeric excess of (R)-dimiracetam (1).

It is to be understood that the "ratio" of (R)-dimiracetam (1) and (S)-dimiracetam (2) as used herein refers to the weight ratio of (R)-dimiracetam (1) and (S)-dimiracetam (2), unless explicitly stated otherwise. If solvates of (R)-dimiracetam (1) and/or (S)-dimiracetam (2) are used, the solvent is thus to be disregarded in this calculation. In other words, the "ratio of (R)-dimiracetam (1) and (S)-dimiracetam (2) is calculated as follows:

$$\text{Ratio of } (R)\text{-dimiracetam (1) and } (S)\text{-dimiracetam (2)} = \frac{\text{amount of } (R)\text{-dimiracetam (1) by weight}}{\text{amount of } (S)\text{-dimiracetam (2) by weight}}$$

As known by the skilled person in the art, the ratio of compounds differing only in chirality, such as in the case of (R)-dimiracetam (1) and (S)-dimiracetam (2), can be determined in a number of ways known in the art, including but not limited to chromatography using a chiral support, polarimetric measurement of the rotation of polarized light, nuclear magnetic resonance spectroscopy using chiral shift reagents, or derivatization of a compound using a chiral compound such as Mosher's acid followed by chromatography or nuclear magnetic resonance spectroscopy. Enantiomers can further be isolated from mixtures by methods known to those skilled in the art, including chiral high-pressure liquid chromatography (HPLC) and direct fractional crystallization of the racemate, i.e. dimiracetam, by chiral co-crystallization techniques, which exploit the formation of specific hydrogen bonding interactions present in co-crystals (see Springuel G R, et al., 2012; and U.S. Pat. No. 6,570,036). Useful co-crystallization partners include enantiomers of mandelic acid, malic acid, tartaric acid and its derivatives; or enantiomers can be prepared by asymmetric syntheses. See, for example, Eliel and Wilen, 1994.

The ratio of (R)-dimiracetam (1) and (S)-dimiracetam (2) (which may also be referred to as the chiral purity) of the inventive composition such as the non-racemic mixture can also be expressed in terms of its enantiomeric excess (ee), typically and preferably as determined by chiral HPLC (see Examples for details), and calculated by the equation:

$$ee=(A_R-A_S)/(A_R+A_S)\times 100\%,$$

wherein $A_R$ is the area of the peak of (R)-3,6,7,7a-tetrahydro-1H-pyrrolo[1,5-a]imidazole-2,5-dione, i.e. (R)-enantiomer (1) of dimiracetam, in the HPLC chromatogram of the sample solution and $A_S$ is the area of the peak of (S)-3,6,7,7a-tetrahydro-1H-pyrrolo[1,5-a]imidazole-2,5-dione, i.e. (S)-enantiomer (2) of dimiracetam, in the HPLC chromatogram of the sample solution.

In this respect, it is noted that, although chiral "purity" is mentioned above, the gist of the present invention is not achieving a high chiral purity of (R)-dimiracetam (1) or (S)-dimiracetam (2). Instead, the gist of the present invention is that a certain range of ratios between (R)-dimiracetam (1) or (S)-dimiracetam (2) leads to a particularly synergistic effect. As opposed to cases in which merely the purity of a compound is to be improved, i.e. where the objective is known, namely one specific compound is to be obtained in a purity of ideally 100%, the present invention is based on a previously unknown ratio of two compounds, namely (R)-dimiracetam (1) and (S)-dimiracetam (2).

The term "pharmaceutically acceptable" indicates that the compound or composition, typically and preferably the solvates, co-crystals or carrier, must be compatible chemically or toxicologically with the other ingredient(s), typically and preferably with the inventive composition, when typically and preferably used in a formulation or when typically and preferably used for treating the animal, preferably the human, therewith. Preferably, the term "pharmaceutically acceptable" indicates that the compound or composition, typically and preferably the solvates, co-crystals or carrier, must be compatible chemically and toxicologically with the other ingredient(s), typically and preferably with the inventive composition, when typically and preferably used in a formulation or when typically and preferably used for treating the animal, preferably the human, therewith. It is noted that pharmaceutical compositions can be formulated by techniques known to the person skilled in the art, such as the techniques published in "Remington: The Science and Practice of Pharmacy", Pharmaceutical Press, 22$^{nd}$ edition.

A "solvate" refers to an association or complex of one or more solvent molecules and either the (R)-enantiomer (1) of dimiracetam or the (S)-enantiomer (2) of dimiracetam. Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

A "co-crystal" refers to a crystalline structure that contains at least two different compounds that are solid in their pure form under ambient conditions. The at least two different compounds may include (R)-dimiracetam (1) and/or (S)-dimiracetam (2) and/or any further components of the composition or excipients of the pharmaceutical composition. Co-crystals are made from neutral molecular species, and all species remain neutral after crystallization; further, typically and preferably, they are crystalline homogeneous phase materials where two or more building compounds are present in a defined stoichiometric ratio. See hereto Wang Y and Chen A, 2013; and Springuel G R, et al., 2012; and U.S. Pat. No. 6,570,036. It to be understood that the (R)-dimiracetam (1) and/or (S)-dimiracetam (2) may be in the form of any polymorph. A variety of co-crystals and techniques for preparing such co-crystals are described in RSC Drug Discovery, Pharmaceutical Salts and Co-crystals, published in 2012 by the Royal Society of Chemistry and edited by Johan Wouters and Luc Quéré, in particular in chapters 15 and 16. Preferred examples of the co-crystal formers are those disclosed in Table 16.1 of this reference. Even more preferred co-crystals include co-crystals of α-hydroxy acids, α-keto acids and/or α-keto amides with the dimiracetam enantiomers in the (R) to (S)-ratios as disclosed herein. Examples of α-hydroxy acids include atrolactic acid, benzilic acid, 4-chloromandelic acid, citric acid, 3,4-dihydroxymandelic acid, ethyl pyruvate, galacturonic acid, gluconolactone, glucuronic acid, glucuronolactone, glycolic acid, 2-hydroxybutanoic acid, 2-hydroxypentanoic acid, 2-hydroxyhexanoic acid, 2-hydroxyheptanoic acid, 2-hydroxyactanoic acid, 2-hydroxynonanoic acid, 2-hydroxydecanoic acid, 2-hydroxyundecanoic acid, 4-hydroxymandelic acid, 3-hydroxy-4-methoxymandelic acid, 4-hydroxy-3-methoxymandelic acid, α-hydroxyarachidonic acid, α-hydroxybutyric acid, α-hydroxyisobutyric acid, α-hydroxylauric acid, α-hydroxymyristic acid, α-hydroxypalmitic acid, α-hydroxystearic acid, 3-(2'-hydroxyphenyl)lactic acid, 3-(4'-hydroxyphenyl)lactic acid, lactic acid, malic acid, mandelic acid, methyllactic acid, methylpyruvate, mucic acid, α-phenylacetic acid, α-phenylpyruvic acid, pyruvic acid, saccharic acid, tartaric acid and tartronic acid. Examples of α-keto acids include 2-ketoethanoic acid (glyoxylic acid), methyl 2-ketoethanoate, 2-ketopropanoic acid (pyruvic acid), methyl 2-ketopropanoate (methyl pyruvate), ethyl 2-ketopropanoate (ethyl pyruvate), propyl 2-ketopropanoate (propyl pyruvate), 2-phenyl-2-ketoethanoic acid (benzoylformic acid), methyl 2-phenyl-2-ketoethanoate (methyl benzoylformate), ethyl 2-phenyl-2-ketoethanoate (ethyl benzoylformate), 3-phenyl-2-ketopropanoic acid (phenylpyruvic acid), methyl 3-phenyl-2-ketopropanoate (methyl phenylpyruvate), ethyl 3-phenyl-2-ketopropanoate (ethyl phenylpyruvate), 2-ketobutanoic acid, 2-ketopentanoic acid, 2-ketohexanoic acid, 2-ketoheptanoic acid, 2-ketooctanoic acid, 2-ketododecanoic acid and methyl 2-ketooctanoate. Examples of α-keto amides include any compounds obtainable by reacting any one of the above examples of α-keto acids with primary or secondary amines.

In a first aspect, the invention provides for a composition comprising (R)-3,6,7,7a-tetrahydro-1H-pyrrolo[1,5-a]imidazole-2,5-dione ((R)-dimiracetam (1)) and (S)-3,6,7,7a-tetrahydro-1H-pyrrolo[1,5-a]imidazole-2,5-dione ((S)-dimiracetam (2)),

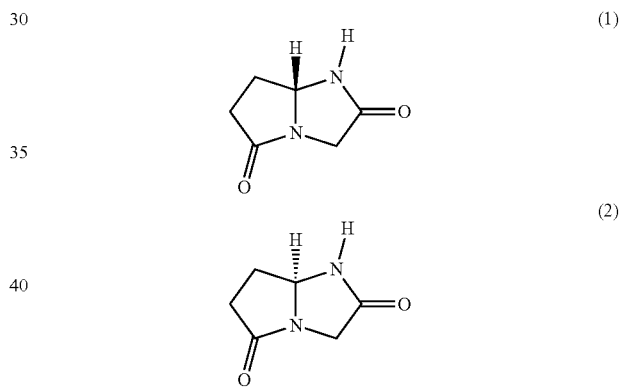

and/or pharmaceutically acceptable solvates or co-crystals thereof,
wherein the enantiomeric excess (ee) of said (R)-dimiracetam (1) is equal to or higher than 30% and lower than or equal to 60%. This composition, as well as any other compositions and pharmaceutical compositions according to the present invention, preferably inhibits NMDA plus glycine-evoked [$^3$H]-D-aspartic acid release from rat spinal synaptosomes by at least about 36%, preferably at least about 40%, more preferably at least about 45%, even more preferably about 50%, at a concentration of about 10 nM. An assay for measuring this parameter is set out in Example 5.

One example of such a composition is a non-racemic mixture of 3,6,7,7a-tetrahydro-1H-pyrrolo[1,5-a]imidazole-2,5-dione and pharmaceutically acceptable solvates or co-crystals thereof, wherein said non-racemic mixture comprises (R)-3,6,7,7a-tetrahydro-1H-pyrrolo[1,5-a]imidazole-2,5-dione ((R)-dimiracetam (1)) and (S)-3,6,7,7a-tetrahydro-1H-pyrrolo[1,5-a]imidazole-2,5-dione ((S)-dimiracetam (2)) in an enantiomeric excess (ee) of said (R)-dimiracetam 1 of higher than or equal to 30% and lower than or equal to 60%.

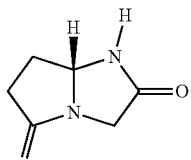

(1)

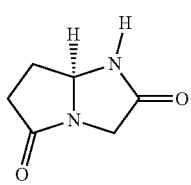

(2)

Typically, the non-solvated or non-co-crystallized compositions are preferred. Further preferred are the non-solvated and non-co-crystallized compositions.

Thus, in a further aspect, the invention provides for a composition of 3,6,7,7a-tetrahydro-1H-pyrrolo[1,5-a]imidazole-2,5-dione, wherein said composition comprises (R)-3,6,7,7a-tetrahydro-1H-pyrrolo[1,5-a]imidazole-2,5-dione ((R)-dimiracetam (1)) and (S)-3,6,7,7a-tetrahydro-1H-pyrrolo[1,5-a]imidazole-2,5-dione ((S)-dimiracetam (2)) in an enantiomeric excess (ee) of said (R)-dimiracetam (1) of higher than or equal to 30% and lower than or equal to 60%.

More preferably, said enantiomeric excess (ee) of said (R)-dimiracetam (1) is higher than or equal to 30% and lower than or equal to about 54%. Even more preferably, said enantiomeric excess (ee) of said (R)-dimiracetam (1) is higher than or equal to 30% and lower than or equal to 54%.

More preferably, said enantiomeric excess (ee) of said (R)-dimiracetam (1) is higher than or equal to about 33% and lower than or equal to about 54%. Even more preferably, said enantiomeric excess (ee) of said (R)-dimiracetam (1) is higher than or equal to 33% and lower than or equal to 54%.

More preferably, said enantiomeric excess (ee) of said (R)-dimiracetam (1) is higher than or equal to 30% and lower than or equal to about 53%. Even more preferably, said enantiomeric excess (ee) of said (R)-dimiracetam (1) is higher than or equal to 30% and lower than or equal to 53%.

More preferably, said enantiomeric excess (ee) of said (R)-dimiracetam (1) is higher than or equal to about 33% and lower than or equal to about 53%. Even more preferably, said enantiomeric excess (ee) of said (R)-dimiracetam (1) is higher than or equal to 33% and lower than or equal to 53%.

Still more preferably, said enantiomeric excess (ee) of said (R)-dimiracetam (1) is higher than or equal to about 33% and lower than or equal to about 50%. Still more preferably, said enantiomeric excess (ee) of said (R)-dimiracetam (1) is higher than or equal to 33% and lower than or equal to 50%.

More preferably, said enantiomeric excess (ee) of said (R)-dimiracetam (1) is higher than or equal to about 30% and lower than or equal to about 50%. Even more preferably, said enantiomeric excess (ee) of said (R)-dimiracetam (1) is higher than or equal to 30% and lower than or equal to 50%.

More preferably, said enantiomeric excess (ee) of said (R)-dimiracetam (1) is higher than or equal to about 35% and lower than or equal to about 54%, and preferably lower than or equal to about 53%. Even more preferably, said enantiomeric excess (ee) of said (R)-dimiracetam (1) is higher than or equal to 35% and lower than or equal to 54%, and preferably lower than or equal to 53%.

More preferably, said enantiomeric excess (ee) of said (R)-dimiracetam (1) is higher than or equal to about 40% and lower than or equal to about 54%, and preferably lower than or equal to about 53%. Even more preferably, said enantiomeric excess (ee) of said (R)-dimiracetam (1) is higher than or equal to 40% and lower than or equal to 54%, and preferably lower than or equal to 53%.

More preferably, said enantiomeric excess (ee) of said (R)-dimiracetam (1) is higher than or equal to about 45% and lower than or equal to about 54%, and preferably lower than or equal to about 53%. Even more preferably, said enantiomeric excess (ee) of said (R)-dimiracetam (1) is higher than or equal to 45% and lower than or equal to 54%, and preferably lower than or equal to 53%.

Still more preferably, said enantiomeric excess (ee) of said (R)-dimiracetam (1) is selected from about 33% about 35%, about 37%, about 39%, about 41%, about 43%, about 45%, about 47% about 50% and about 53%. Still more preferably, said enantiomeric excess (ee) of said (R)-dimiracetam (1) is selected from 33%, 35%, 37%, 39%, 41%, 43%, 45%, 47%, 50% and 53%.

Even still more preferably, said enantiomeric excess (ee) of said (R)-dimiracetam (1) is selected from about 50%. Even still more preferably, said enantiomeric excess (ee) of said (R)-dimiracetam (1) is 50%.

As known to the skilled person, instead of the enantiomeric excess, the ratio of (R)-dimiracetam (1) to (S)-dimiracetam (2) may be referred to. Preferred ranges for the ratio of (R)-dimiracetam (1) to (S)-dimiracetam (2) are 2:1 to 3.5:1, preferably 2:1 to 3.3:1, more preferably 2.0:1.0 to 3.3:1.0, even more preferably 2.00:1.00 to 3.30:1.00. Further preferred ranges are 2.0:1.0 to 3.25:1.0, 2.00:1.00 to 3.25:1.00, 2:1 to 3:1, 2.0:1.0 to 3.0:1.0 and 2.00:1.00 to 3.00:1.00. Further preferred ranges include 2.3:1 to 3.3:1, 2.6:1 to 3.3:1, 2.7:1 to 3.2:1, 2.8:1 to 3.2:1, 2.9:1 to 3.1:1 as well as 3:1 and 3.0:1.0. Other preferred ranges include 2.1:1 to 2.9:1, 2.2:1 to 2.8:1, 2.3:1 to 2.7:1, 2.4:1 to 2.6:1, as well as 2.5:1 and 2.5:1.0.

In a further aspect, the invention provides for a pharmaceutical composition comprising the composition of the invention and a pharmaceutically acceptable carrier.

In a further aspect, the invention provides for a kit of parts comprising (R)-dimiracetam (1) and (S)-dimiracetam (2) and instructions for combining (R)-dimiracetam (1) and (S)-dimiracetam (2) to obtain an enantiomeric excess (ee) of said (R)-dimiracetam (1) of equal to or higher than 30% and lower than or equal to 60%. In the following, it is to be understood that the kit according to the present invention may alternatively be used, whenever the use of the composition of the present invention is described. The skilled person will understand that the components of the kit may be combined before administration, which is preferred, or the components of the kit may be administered separately. In the latter case, the components of the kit are typically to be administered within a time range of at most 30 minutes in order to achieve the effects of the present invention.

In again a further aspect, the invention provides for the composition of the invention or the pharmaceutical composition of the invention or the kit of the invention for use as a medicament.

In again a further aspect, the invention provides for the composition of the invention or the pharmaceutical composition of the invention or the kit of the invention for use in the treatment or prevention of a large number of diseases and disorders such as set out in the following:

a) for the prevention or the treatment of positive symptoms of peripheral neuropathy, including cold-sensitivity, tingling, burning, or aching sensations, such as those associated with chemotherapy, antiblastic therapy, viral infection and viral treatment, post-herpetic neuralgia, osteonecrosis, trigeminal neuralgia, or diabetic peripheral neuropathy, to include the primary allodynia, secondary allodynia, or other pains or discomforts associated with sensitization of the spinal cord or higher brain structures or neuronal pathways;

b) for the prevention or the treatment of pain, including bone and joint pain, osteonecrosis pain, repetitive motion pain, dental pain, dysmenorrheal pain, cancer pain, myofascial pain, surgical pain, perioperative pain, and postsurgical pain syndromes such as post-mastectomy syndrome, post-thoracotomy syndrome, or stump pain, as well as pain associated with angina, neuroma pain, complex regional pain syndrome, chronic pelvic pain, chronic lower back pain;

c) for the prevention or the treatment of inflammatory pain, such as osteoarthritis, rheumatoid arthritis, rheumatic disease, chronic arthritic pain and related neuralgias, tenosynovitis and gout;

d) for the prevention or the treatment of neuropathic pain, such as chemotherapy-induced pain, post-traumatic injury pain, crush pain, painful traumatic mononeuropathy, painful polyneuropathy, pain resulting from spinal injury, lumbago, nerve compression or entrapment, sacral pain, trigeminal neuralgia, migraine and migraine headache, post-herpetic neuralgia, phantom limb pain, post-herpetic pain, diabetic neuropathy, central pain syndrome caused a lesion at any level of the peripheral nervous system;

e) for the prevention or the treatment of neuropsychiatric disorders. Examples of neuropsychiatric disorders include schizophrenia, psychosis including schizophrenia, schizophreniform disorder, schizoaffective disorder, delusional disorder, brief psychotic disorder, substance-related disorder, paranoid schizophrenia, disorganized schizophrenia, catatonic schizophrenia or undifferentiated schizophrenia, substance-induced psychotic disorder, substance-related disorders and addictive behaviors;

f) epilepsy and other seizures, both focal and generalized;

g) obesity or other eating disorders associated with excessive food intake, bulimia nervosa;

h) cerebral deficits subsequent to stroke, brain edema, cerebral ischemia, cerebral hemorrhage, neurodegenerative diseases, cardiac bypass surgery and grafting, perinatal hypoxia, cardiac arrest, and hypoglycemic cerebral damage;

i) sleep disorders, such as insomnia, narcolepsy, or restless leg disorder;

j) anxiety disorders, such as affective disorder, panic attacks, panic disorder, acute stress disorder, agoraphobia, generalized anxiety disorder, obsessive-compulsive disorder, posttraumatic stress disorder, separation anxiety disorder, social phobia, specific phobia, substance-induced anxiety disorder;

k) mood disorders, such as depression, anhedonia, unipolar depression, bipolar disorder, psychotic depression;

l) substance addiction, drug dependence, tolerance, dependence or withdrawal from substances including alcohol, amphetamines, cannabis, cocaine, hallucinogens, inhalants, nicotine, opioids, phencyclidine, sedatives, hypnotics or anxiolytics;

m) impaired cognitive function, such as age related cognitive decline or cognitive disorders such as the different types of dementia associated with Alzheimer's disease, ischemia, trauma, vascular problems or stroke, HIV disease, Parkinson's disease, Huntington's disease, Pick's disease, Creutzfeldt-Jacob disease, chemotherapy, perinatal hypoxia, other general medical conditions or substance abuse;

n) Parkinson's disease, including drug-induced parkinsonism, or post-encephalitic parkinsonism;

o) attention deficit disorders, such as attention-deficit hyperactivity disorder (ADHD), obsessive-compulsive disorder, phobia, posttraumatic stress syndrome, autism and autism-spectrum disorders, impulse control disorder;

p) tinnitus, presbycusis;

q) to enhance learning and memory;

r) for the prevention or for the treatment of inherited or sporadic motor neuron disorders. Examples thereof include amyotrophic lateral sclerosis, primary lateral sclerosis, progressive muscular atrophy, progressive bulbar palsy, Friedrich's ataxia, fragile X syndrome;

s) for the prevention or for the treatment of movement disorders. Examples thereof include dystonia, chorea, including Huntington's chorea, Parkinson's-related dystonia, Creutzfeldt-Jakob disease, progressive supranuclear palsy, multiple system atrophy, corticobasal degeneration, basal ganglia calcification;

t) for akinesias such as akinetic-rigid syndromes, u) for dyskinesias such as medication-induced parkinsonism such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor, including rest tremor, postural tremor and intention tremor, chorea (such as Sydenham's chorea, Huntington's disease, benign hereditary chorea, neuroacanthocytosis, symptomatic chorea, drug-induced chorea and hemiballism), generalized or focal myoclonus, tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia), muscular spasms and disorders associated with muscular spasticity or weakness including tremors;

v) and for urinary incontinence, multiple system atrophy, tuberous sclerosis, olivo-ponto-cerebellar atrophy, cerebral palsy, drug-induced optic neuritis, ischemic retinopathy, diabetic retinopathy, glaucoma, spasticity, myoclonus, and Tourette's syndrome-associated dyskinesias.

It is to be understood that the above list of diseases is only given as specific examples and is not to be interpreted as limiting the present invention. Among the above, preferred are one or more selected from a), e), q), r), and s).

The disease or disorder is typically and preferably selected from peripheral sensory neuropathy, preferably peripheral neuropathic pain and other symptoms of peripheral sensory neuropathy; and neuropsychiatric conditions, such as seizure; depression; or cognitive impairment; and motoneuron diseases, such as amyotrophic lateral sclerosis.

Furthermore, the compositions of the present invention can also be used to enhance learning and memory in healthy subjects, e.g. in the form of a non-therapeutic use.

In again a further aspect, the invention provides for a method for the treatment and/or prevention of a disease or disorder, wherein the disease or disorder is typically and preferably selected from peripheral sensory neuropathy, preferably peripheral neuropathic pain and other symptoms of peripheral sensory neuropathy; and neuropsychiatric conditions, such as seizure; depression; or cognitive impairment; and motoneuron diseases, such as amyotrophic lateral sclerosis, wherein said method comprises administration of the composition of the invention or the pharmaceutical composition of the invention or the kit of the invention.

It is also part of the invention to provide a method for the treatment of a disease or disorder, wherein a therapeutically effective amount of the composition of the invention or the pharmaceutical composition of the invention or the kit of the invention is administered to an animal, preferably human, in need thereof. The term "therapeutically effective amount" here refers to that amount sufficient to modulate one or more of the symptoms of the condition or disease being treated, preferably between 10 mg and 3000 mg per administration given once daily or twice daily or three times daily by the oral route. It is furthermore also a part of the invention to provide a method for the prevention of a disease or disorder, wherein a therapeutically effective amount of the composition of the invention or the pharmaceutical composition of the invention or the kit of the invention is administered to an animal, preferably human, reasonably expected to be in need thereof. The term "therapeutically effective amount" here refers to that amount sufficient to modulate one or more of the expected symptoms of the condition or disease to be avoided, preferably between 10 mg and 3000 mg per administration given once daily or twice daily or three times daily by the oral route.

In again a further aspect, the invention provides for the use of the composition of the invention or the pharmaceutical composition of the invention or the kit of the invention in the manufacture of a medicament for use in the treatment and/or prevention of a disease or disorder, wherein the disease or disorder is typically and preferably selected from peripheral sensory neuropathy, preferably peripheral neuropathic pain and other symptoms of peripheral sensory neuropathy; and neuropsychiatric conditions, such as seizure; depression; or cognitive impairment; and motoneuron diseases, such as amyotrophic lateral sclerosis.

It is also part of the present invention to administer the inventive composition or the inventive pharmaceutical composition in association with active principles and active agents, respectively, which present as side effects the insurgence of peripheral neuropathic pain and other symptoms of peripheral neuropathy, in particular with antitumor and antiviral drugs. The composition or the pharmaceutical composition or the kit is preferably used alone or with at least one antitumor drug or at least one antiviral drug. More preferably, the composition or the pharmaceutical composition or the kit is used alone. More preferably, the composition or the pharmaceutical composition or the kit is used with at least one antitumor drug. Alternatively, preferably, the composition or the pharmaceutical composition or the kit is used with at least one antiviral drug.

It is furthermore preferred that the composition or the pharmaceutical composition or the kit is administered in association with at least one antitumor drug or with at least one antiviral drug, wherein said associated administration of said composition or said pharmaceutical composition with said at least one antitumor drug or with said at least one antiviral drug is concurrent, simultaneous, sequential or separate.

Non-limiting examples of such antitumor drugs are selected from the group consisting of a kinase inhibitor, a proteasome inhibitor, a taxane, a vinca alkaloid, and a platinum salt. Non-limiting examples of such antiviral drugs are selected from a nucleoside analog or a nucleotide analog. It is furthermore preferred that said antitumor drug is selected from the group consisting of a kinase inhibitor, a proteasome inhibitor, a taxane, a vinca alkaloid, and a platinum salt. Said antitumor drug is preferably selected from sorafenib, sunitinib, afatinib, axitinib, vandetanib, vemurafenib, ixazomib, bortezomib, paclitaxel, docetaxel, cabazitaxel, vincristine, vinblastine, vindesine, vinorelbine, nedaplatin, lobaplatin, picoplatin, satraplain, cisplatin, carboplatin, and oxaliplatin. Said antiviral drug is preferably selected from zalcitabine, didanosine, stavudine and zidovudine.

The composition or the pharmaceutical composition or the kit is preferably used with at least one antiviral drug, wherein preferably said antiviral drug is selected from a nucleoside or nucleotide, and wherein further preferably said antiviral drug is selected from zalcitabine, didanosine, stavudine or zidovudine.

Said disease or disorder is preferably seizure. Alternatively, said disease or disorder is preferably depression. Further preferably, said disease or disorder is cognitive impairment. Even more preferably, said disease or disorder is peripheral sensory neuropathy. Still more preferably, said disease or disorder is peripheral neuropathic pain.

Said disease or disorder is more preferably peripheral sensory neuropathy, wherein said peripheral sensory neuropathy is selected from the group consisting of (i) diabetic neuropathy, (ii) post-herpetic neuropathy, (iii) lumbago, (iv) sacral pain, (v) surgical pain, (vi) crush injury, (vii) spinal injury, (viii) complex regional pain syndrome, (ix) phantom limb sensations, (x) peripheral sensory neuropathy associated with osteoarthritis, (xi) peripheral sensory neuropathy associated with rheumatoid arthritis, (xii) peripheral sensory neuropathy associated with autoimmune osteoarthrosis, (xiii) cephalea (xiv) fibromyalgia, (xv) peripheral sensory neuropathy induced by antiblastic therapies, (xvi) peripheral sensory neuropathy induced by a chemotherapeutic agent, (xvii) peripheral sensory neuropathy associated with visceral injury, (xviii) peripheral sensory neuropathy associated with osteonecrosis, (xix) peripheral sensory neuropathy associated with human immunodeficiency virus infection and (xx) peripheral sensory neuropathy induced by an antiviral agent.

Said disease or disorder is preferably peripheral sensory neuropathy, wherein said peripheral sensory neuropathy is selected from the group consisting of (i) diabetic neuropathy, (ii) post-herpetic neuropathy, (iii) lumbago, (iv) sacral pain, (v) surgical pain, (vi) crush injury, (vii) spinal injury, (viii) complex regional pain syndrome, (ix) phantom limb sensations, (x) peripheral sensory neuropathy associated with osteoarthritis, (xi) peripheral sensory neuropathy associated with rheumatoid arthritis, (xii) peripheral sensory neuropathy associated with autoimmune osteoarthrosis, (xiii) cephalea (xiv) fibromyalgia, (xv) peripheral sensory neuropathy induced by antiblastic therapies, (xvi) peripheral sensory neuropathy induced by a chemotherapeutic agent, (xvii) peripheral sensory neuropathy associated with visceral injury, (xviii) peripheral sensory neuropathy associated with osteonecrosis, (xix) peripheral sensory neuropathy associated with human immunodeficiency virus infection, (xx) peripheral sensory neuropathy induced by an antiviral agent and (xxi) peripheral neuropathic pain.

Said disease or disorder is further preferably peripheral sensory neuropathy, wherein said peripheral sensory neuropathy is diabetic neuropathy. Said disease or disorder is even more preferably peripheral sensory neuropathy, wherein said peripheral sensory neuropathy is post-herpetic neuropathy. Said disease or disorder is preferably peripheral sensory neuropathy, wherein said peripheral sensory neuropathy is lumbago. Said disease or disorder is further preferably peripheral sensory neuropathy, wherein said peripheral sensory neuropathy is sacral pain. Said disease or disorder is further preferably peripheral sensory neuropathy, wherein said peripheral sensory neuropathy is surgical pain. Said disease or disorder is further preferably peripheral sensory neuropathy, wherein said peripheral sensory neuropathy is crush injury. Said disease or disorder is further preferably peripheral sensory neuropathy, wherein said peripheral sensory neuropathy is spinal injury. Said disease or disorder is further preferably peripheral sensory neuropathy, wherein said peripheral sensory neuropathy is complex regional pain syndrome. Said disease or disorder is further preferably peripheral sensory neuropathy, wherein said peripheral sensory neuropathy is phantom limb sensations. Said disease or disorder is further preferably peripheral sensory neuropathy, wherein said peripheral sensory neuropathy is peripheral sensory neuropathy associated with osteoarthritis. Said disease or disorder is further preferably peripheral sensory neuropathy, wherein said peripheral sensory neuropathy is peripheral sensory neuropathy associated with rheumatoid arthritis. Said disease or disorder is further preferably peripheral sensory neuropathy, wherein said peripheral sensory neuropathy is peripheral sensory neuropathy associated with autoimmune osteoarthrosis. Said disease or disorder is further preferably peripheral sensory neuropathy, wherein said peripheral sensory neuropathy is cephalea. Said disease or disorder is further preferably peripheral sensory neuropathy, wherein said peripheral sensory neuropathy is fibromyalgia. Said disease or disorder is still more preferably peripheral sensory neuropathy, wherein said peripheral sensory neuropathy is peripheral sensory neuropathy induced by antiblastic therapies. Said disease or disorder is still more preferably peripheral sensory neuropathy, wherein said peripheral sensory neuropathy is peripheral sensory neuropathy induced by a chemotherapeutic agent. Said disease or disorder is still more preferably peripheral sensory neuropathy, wherein said peripheral sensory neuropathy is peripheral sensory neuropathy associated with visceral injury. Said disease or disorder is still more preferably peripheral sensory neuropathy, wherein said peripheral sensory neuropathy is peripheral sensory neuropathy associated with osteonecrosis. Said disease or disorder is still more preferably peripheral sensory neuropathy, wherein said peripheral sensory neuropathy is peripheral sensory neuropathy associated with human immunodeficiency virus infection. Said disease or disorder is still more preferably peripheral sensory neuropathy, wherein said peripheral sensory neuropathy is peripheral sensory neuropathy induced by an antiviral agent. Said disease or disorder is further preferably peripheral sensory neuropathy, wherein said peripheral sensory neuropathy is peripheral neuropathic pain.

Said peripheral sensory neuropathy is preferably selected from peripheral sensory neuropathy induced by a chemotherapeutic agent or peripheral sensory neuropathy induced by an antiviral agent.

Said disease or disorder is still more preferably peripheral sensory neuropathy induced by a chemotherapeutic agent, wherein typically and preferably said chemotherapeutic agent is selected from the group consisting of a kinase inhibitor, a proteasome inhibitor, a taxane, a vinca alkaloid and a platinum salt. Still more preferably, said disease or disorder is peripheral sensory neuropathy induced by a chemotherapeutic agent, wherein said chemotherapeutic agent is selected from the group consisting of a kinase inhibitor, a proteasome inhibitor, a taxane, a vinca alkaloid and a platinum salt. Still more preferably, said disease or disorder is peripheral sensory neuropathy induced by a chemotherapeutic agent, wherein said chemotherapeutic agent is selected from the group consisting of sorafenib, sunitinib, afatinib, axitinib, vandetanib, vemurafenib, ixazomib, bortezomib, paclitaxel, docetaxel, cabazitaxel, vincristine, vinblastine, vindesine, vinorelbine, nedaplatin, lobaplatin, picoplatin, satraplain, cisplatin, carboplatin, or oxaliplatin. Said disease or disorder is still more preferably peripheral sensory neuropathy induced by a chemotherapeutic agent, wherein said chemotherapeutic agent is selected from the group consisting of sorafenib, vincristine, paclitaxel, or oxaliplatin. Very preferably, said peripheral sensory neuropathy is induced by a chemotherapeutic agent, wherein said chemotherapeutic agent is sorafenib, paclitaxel, vincristine, cisplatin, carboplatin or oxaliplatin.

Further preferably, said disease or disorder is peripheral sensory neuropathy induced by an antiviral agent, wherein preferably said antiviral agent is a nucleoside reverse transcriptase inhibitor. Still more preferably, said disease or disorder is peripheral sensory neuropathy induced by an antiviral agent, wherein said antiviral agent is selected from zalcitabine, didanosine, stavudine or zidovudine. Still more preferably, said disease or disorder is peripheral sensory neuropathy induced by zalcitabine Preferably, said chemotherapy-induced peripheral sensory neuropathy entails symptoms of allodynia or dysesthesia, more preferably allodynia or dysesthesia of the hands or feet, and further preferably allodynia or dysesthesia of the hands or feet induced by sorafenib, by vincristine, by paclitaxel, or by carboplatin, cisplatin, or oxaliplatin.

Still more preferably, said peripheral sensory neuropathy is associated with pain, paresthesias, dysesthesias or allodynia.

Further preferably, the inventive composition or the inventive pharmaceutical composition may be administered prophylactically, starting before the antitumoral chemotherapeutic principle has induced peripheral sensory neuropathy and its attendant symptoms.

Further preferably, the inventive composition or the inventive pharmaceutical composition may be administered intermittently. Furthermore it is a preferred in the present invention that the inventive composition or the inventive pharmaceutical composition may be administered in synchrony with repeated cycles of an antitumoral chemotherapeutic principle.

The dosage will depend on the route of administration, the severity of the disease, age and weight of the patient or subject and other factors normally considered by the attending physician, when determining the individual regimen and dosage level for a particular patient or subject.

The composition or pharmaceutical composition of the invention may be administered via any route, including oral, intramuscular, subcutaneous, topical, transdermal, intranasal, intravenous, sublingual or intrarectal administration. Typically and preferably, the pharmaceutical composition of the invention is administered in a single dosage unit once-daily, twice-daily or three times-daily via the oral route, and most preferably once-daily or twice-daily. In the most preferred embodiment, the composition or pharmaceutical composition of the invention is administered twice daily.

Typically and preferably, the oral dose of the inventive composition or the inventive pharmaceutical composition is between 10 mg and 3000 mg per administration, more preferably between 20 mg to 2000 mg per administration, again more preferably between 50 mg and 1000 mg per administration. Typically and preferably, said composition or said pharmaceutical composition is administered orally twice daily in a dose of between 10 mg and 3000 mg per administration, more preferably between 20 mg to 2000 mg per administration, again more preferably between 50 mg and 1000 mg per administration.

The pharmaceutical composition of the invention may be prepared by mixing suitably selected and pharmaceutically acceptable excipients, vehicles, adjuvants, additives, surfactants, desiccants or diluents known to those well-skilled in the art, and can be suitably adapted for oral, parenteral or topical administration. Typically and preferably the pharmaceutical composition of the invention is administered in the form of a tablet, capsule, sachets, powder, granule, pellet, oral or parenteral solution, suspension, suppository, ointment, cream, lotion, gel, paste and/or may contain liposomes, micelles and/or microspheres.

The pharmaceutically acceptable carrier of the pharmaceutical composition of the invention is without limitation any pharmaceutically acceptable excipient, vehicle, adjuvant, additive, surfactant, desiccant or diluent. Suitable pharmaceutically acceptable carriers are magnesium carbonate, magnesium stearate, talc, lactose, sugar, pectin, dextrin, starch, tragacanth, methyl cellulose, sodium carboxymethyl cellulose, a low-melting wax, cocoa butter. Pharmaceutically acceptable carriers of the invention can be solid, semi-solid or liquid.

Tablets, capsules or sachets for oral administration are usually supplied in dosage units and may contain conventional excipients, such as binders, fillers, diluents, tableting agents, lubricants, detergents, disintegrants, colorants, flavors and wetting agents. Tablets may be coated in accordance to methods well known in the art. Suitable fillers include or are preferably cellulose, mannitol, lactose and similar agents. Suitable disintegrants include or are preferably starch, polyvinyl pyrrolidone and starch derivatives such as sodium starch glycolate. Suitable lubricants include or are preferably, for example, magnesium stearate. Suitable wetting agents include or are preferably sodium lauryl sulfate. These solid oral compositions can be prepared with conventional mixing, filling or tableting methods. The mixing operations can be repeated to disperse the active agent in compositions containing large quantities of fillers. These operations are conventional.

The oral liquid compositions can be provided in the form of, for example, aqueous solutions, emulsions, syrups or elixirs or in the form of a dry product to be reconstituted with water or with a suitable liquid carrier at the time of use. The liquid compositions can contain conventional additives, such as suspending agents, for example sorbitol, syrup, methylcellulose, gelatin, hydroxyethyl cellulose, carboxymethyl cellulose, aluminum stearate gel or hydrogenated edible fats; emulsifying agents, for example lecithin, sorbitan monooleate, or acacia; non aqueous carriers (which can include edible oil), for example almond oil, fractionated coconut oil, oily esters, such as glycerin esters, propylene glycol or ethyl alcohol; preservatives, for example methyl or propyl p-hydroxybenzoate or sorbic acid and if desired, conventional flavors or colorants. Oral formulations may also include or may be formulated as conventional formulations, such as tablets or granules. For parenteral administration, liquid dosage units can be prepared containing the inventive composition and a sterile carrier.

Oral formulations may optionally further include taste-masking components to optimize the taste perception of the oral formulation. Examples of such taste-masking components may be citrus-, licorice-, mint-, grape-, black currant- or eucalyptus-based flavorants known to those well-skilled in the art.

The parenteral solutions are normally prepared by dissolving the compound in a carrier and sterilizing by filtration, before filling suitable vials or ampoules and sealing.

Adjuvants, such as local anesthetics, preservatives and buffering agents can be added to the pharmaceutical composition. In order to increase stability, the composition can be frozen after filling the vial and the water removed under vacuum. A surfactant or humectant can be advantageously included in the pharmaceutical composition in order to facilitate uniform distribution of the inventive composition.

Topical formulations include or are preferably ointments, creams, lotions, gels, gums, solutions, pastes or may contain liposomes, micelles or microspheres.

Subjects to be treated by the composition or pharmaceutical composition of the invention are humans and animals. Preferred animals are domestic and farm animals, including but not limited to guinea pig, rabbit, horse, donkey, camel, cow, sheep, goat, pig, cat, dog and parrot. More preferred subjects are mammals, again more preferably humans.

In again a further aspect, the invention provides for an article of manufacture comprising the composition of the invention or the pharmaceutical composition of the invention or the kit of the invention, a container or package and a written description and administration instruction such as a package insert.

It is further envisaged that compositions of (R)-dimiracetam or (S)-dimiracetam with other racetams such as aniracetam, brivaracetam, cebaracetam, coluracetam, doliracetam, dupracetam, etiracetam/levetiracetam, fasoracetam, imuracetam, methylphenylpiracetam, nebracetam, nefiracetam, omberacetam (Noopept), oxiracetam, phenylpiracetam, phenylpiracetam hydrazide, piracetam, pramiracetam, rolipram, rolziracetam and/or seletracetam may also be used to prepare synergistic mixtures and compositions, in particular if the ratio of (R)-dimiracetam or (S)-dimiracetam and the other racetam, or an enantiomer of the other racetam, are chosen within the ranges disclosed herein for the mixtures of (R)-dimiracetam and (S)-dimiracetam.

It is further envisaged that compositions of (R)-dimiracetam or (S)-dimiracetam with other derivatives of dimiracetam, such as those disclosed in U.S. Pat. No. 7,544,705 or in U.S. Pat. No. 8,334,286, may also be used to prepare synergistic mixtures and compositions, in particular if the ratio of (R)-dimiracetam and the dimiracetam-like compound, or an enantiomer of the dimiracetam-like compound, are chosen within the ranges disclosed herein for the mixtures of (R)-dimiracetam and (S)-dimiracetam.

The present invention also relates to a method of treating and/or preventing a disease, injury, or disorder, comprising: administering to a subject the composition of claim 1, wherein the disease, injury, or disorder is peripheral sensory neuropathy, seizure, depression, or cognitive impairment. In this method, the disease, injury, or disorder is preferably peripheral sensory neuropathy, a neuropsychiatric disorder, a motoneuron disorder, or a movement disorder. More preferably, the disease, injury, or disorder is peripheral sensory neuropathy. The peripheral sensory neuropathy is preferably peripheral neuropathic pain. The peripheral sensory neuropathy is preferably selected from diabetic neuropathy, post-herpetic neuropathy, lumbago, sacral pain, surgical pain, crush injury, spinal injury, complex regional pain syndrome, phantom limb sensations, peripheral sensory neuropathy associated with osteoarthritis, peripheral sensory neuropathy associated with rheumatoid arthritis, peripheral sensory neuropathy associated with autoimmune osteoarthrosis, cephalea, fibromyalgia, peripheral sensory neuropathy induced by antiblastic therapies, peripheral sensory neuropathy induced by a chemotherapeutic agent, peripheral sensory neuropathy associated with visceral injury, peripheral sensory neuropathy associated with osteonecrosis, peripheral sensory neuropathy associated with human immunodeficiency virus infection, peripheral neuropathic pain, or peripheral sensory neuropathy induced by an antiviral agent. In some instances, the peripheral sensory neuropathy is peripheral sensory neuropathy induced by a chemotherapeutic agent or peripheral sensory neuropathy induced by an antiviral agent. In certain instances, the peripheral sensory neuropathy is peripheral sensory neuropathy induced by a chemotherapeutic agent, wherein the chemotherapeutic agent is selected from the group consisting of a kinase inhibitor, a proteasome inhibitor, a taxane, a vinca alkaloid, and a platinum salt, and wherein preferably the chemotherapeutic agent is selected from sorafenib, sunitinib, afatinib, axitinib, vandetanib, vemurafenib, ixazomib, bortezomib, paclitaxel, docetaxel, cabazitaxel, vincristine, vinblastine, vindesine, vinorelbine, nedaplatin, lobaplatin, picoplatin, satraplain, cisplatin, carboplatin, and oxaliplatin. In some instances, the peripheral sensory neuropathy is peripheral sensory neuropathy induced by an antiviral agent, wherein the antiviral agent is a nucleoside reverse transcriptase inhibitor. In some instances, the nucleoside reverse transcriptase inhibitor is zalcitabine, didanosine, stavudine, or zidovudine.

In some instances, the method further comprises administering an antitumor drug, wherein the antitumor drug is selected from the group consisting of a kinase inhibitor, a proteasome inhibitor, a taxane, a vinca alkaloid, and a platinum salt. In some instances, the antitumor drug is selected from the group consisting of sorafenib, sunitinib, afatinib, axitinib, vandetanib, vemurafenib, ixazomib, bortezomib, paclitaxel, docetaxel, cabazitaxel, vincristine, vinblastine, vindesine, vinorelbine, nedaplatin, lobaplatin, picoplatin, satraplain, cisplatin, carboplatin, and oxaliplatin. In some instances, the method further comprises administering an antiviral drug, wherein the antiviral drug is a nucleoside or a nucleotide. In some instances, the antiviral drug is zalcitabine, didanosine, stavudine, or zidovudine. In some instances, the composition is administered orally twice daily in a dose of between 10 mg and 3000 mg per administration, between 20 mg to 2000 mg per administration, or between 50 mg and 1000 mg per administration.

The present invention furthermore relates to a method of enhancing learning and memory, comprising administering to a subject the composition of the present invention as described herein. In some instances of this method, the subject is a healthy subject.

The non-patent references cited herein are abbreviated by first author accompanied by the year of publication. The complete citations are listed in the following.

Attal N, Cruccu G, Baron R, Haanpää M, Hansson P, Jensen T S, Nurmikko T; European Federation of Neurological Societies. EFNS guidelines on the pharmacological treatment of neuropathic pain: 2010 revision. *Eur J Neurol.* 2010 September; 17(9): 1113-e88. PMID: 20402746

Bradford M M. A rapid and sensitive method for the quantitation of microgram quantities of protein utilizing the principle of protein-dye binding. *Anal Biochem.* 1976 May 7; 72:248-54. PMID: 942051

Bril V, England J, Franklin G M, Backonja M, Cohen J, Del Toro D, Feldman E, Iverson D J, Perkins B, Russell J W, Zochodne D; American Academy of Neurology; American Association of Neuromuscular and Electrodiagnostic Medicine; American Academy of Physical Medicine and Rehabilitation. Evidence-based guideline: Treatment of painful diabetic neuropathy: report of the American Academy of Neurology, the American Association of Neuromuscular and Electrodiagnostic Medicine, and the American Academy of Physical Medicine and Rehabilitation. *Neurology.* 2011 May 17; 76(20):1758-65. Erratum in: Neurology. 2011 Aug. 9; 77(6):603. PMID: 21482920

Camilleri P, Eggleston D, Farina C, Murphy J A, Pfeiffer U, Pinza M, Senior L A. Chiral high-performance liquid chromatography of some related bicyclic lactams. *Journal of Chromatography A,* 654 (1993) 207-213.

Cavaletti G, Tredici G, Petruccioli M G, Donde E, Tredici P, Marmiroli P, Minoia C, Ronchi A, Bayssas M, Etienne G G. Effects of different schedules of oxaliplatin treatment on the peripheral nervous system of the rat. *Eur J Cancer.* 2001 December; 37(18):2457-63. PMID: 11720843

Christensen D, Idanpaan-Heikkila J J, Guilbaud G, Kayser V. The antinociceptive effect of combined systemic administration of morphine and the glycine/NMDA receptor antagonist, (+)-HA966 in a rat model of peripheral neuropathy. *Br J Pharmacol.* 1998 December; 125(8): 1641-50. Erratum in: *Br J Pharmacol* 1999 April; 126 (8):1881. PMID: 9886755

Dubinsky R M, Kabbani H, El-Chami Z, Boutwell C, Ali H; Quality Standards Subcommittee of the American Academy of Neurology. Practice parameter: treatment of postherpetic neuralgia: an evidence-based report of the Quality Standards Subcommittee of the American Academy of Neurology. Neurology. 2004 Sep. 28; 63(6):959-65. PMID: 15452284

Di Cesare Mannelli L, Maresca M, Farina C, Scherz M W, Ghelardini C. A model of neuropathic pain induced by sorafenib in the rat: Effect of dimiracetam. Neurotoxicology. 2015a September; 50:101-7. PMID: 26254739

Di Cesare Mannelli L, Micheli L, Farina C, Scherz M, and Ghelardini C. Effects of dimiracetam on oxaliplatin-induced hyperalgesia and allodynia in the rat. *Journal of Clinical Oncology* 2015b 33:15_suppl, e20650-e20650.

Eliel E L, Wilen S H. Stereochemistry of Organic Compounds, Wiley-Interscience, New York (1994). ISBN: 978-0-471-01670-0

Fariello R G, Ghelardini C, Di Cesare Mannelli L, Bonanno G, Pittaluga A, Milanese M, Misiano P, Farina C. Broad spectrum and prolonged efficacy of dimiracetam in models of neuropathic pain. *Neuropharmacology.* 2014 June; 81:85-94. PMID: 24486381

Fariello R G, Ghelardini C, Di Cesare Manneli L, Zanardelli M, Farina C. Antidepressant-like activity of dimiracetam (NT-11624) in the rat forced swimming test. Program No. 789.08/EE25. 2011 *Neuroscience Meeting Planner.* Washington, D.C.: Society for Neuroscience, 2011. Online.

Fernihough J, Gentry C, Malcangio M, Fox A, Rediske J, Pellas T, Kidd B, Bevan S, Winter J. Pain related behaviour in two models of osteoarthritis in the rat knee. *Pain.* 2004; November; 112(1-2):83-93. PMID: 15494188

Finnerup N B, Attal N, Haroutounian S, McNicol E, Baron R, Dworkin R H, Gilron I, Haanpää M, Hansson P, Jensen T S, Kamerman P R, Lund K, Moore A, Raja S N, Rice A S, Rowbotham M, Sena E, Siddall P, Smith B H, Wallace M. Pharmacotherapy for neuropathic pain in adults: a systematic review and meta-analysis. *Lancet Neurol.* 2015 February; 14(2):162-73. PMID: 25575710

Gronseth G, Cruccu G, Alksne J, Argoff C, Brainin M, Burchiel K, Nurmikko T, Zakrzewska J M. Practice parameter: the diagnostic evaluation and treatment of trigeminal neuralgia (an evidence-based review): report of the Quality Standards Subcommittee of the American Academy of Neurology and the European Federation of Neurological Societies. *Neurology.* 2008 Oct. 7; 71(15): 1183-90. PMID: 18716236

Guingamp C, Gegout-Pottie P, Philippe L, Terlain B, Netter P, Gillet P. Mono-iodoacetate-induced experimental osteoarthritis: a dose-response study of loss of mobility, morphology, and biochemistry. *Arthritis Rheum.* 1997 September; 40(9):1670-9. PMID: 9324022

Guzman R E, Evans M G, Bove S, Morenko B, Kilgore K. Mono-iodoacetate-induced histologic changes in subchondral bone and articular cartilage of rat femorotibial joints: an animal model of osteoarthritis. ToxicolPathol. 2003; 31(6):619-24. PMID: 14585729

Latremoliere A, Woolf C J. Central sensitization: a generator of pain hypersensitivity by central neural plasticity. *J Pain.* 2009 September; 10(9):895-926. PMID: 19712899.

Marieb E N, Wilhelm P B & Mallat J B, eds. Human Anatomy, 8th edition. Pearson, London (2017).

Moulin D, Boulanger A, Clark A J, Clarke H, Dao T, Finley G A, Furlan A, Gilron I, Gordon A, Morley-Forster P K, Sessle B J, Squire P, Stinson J, Taenzer P, Velly A, Ware M A, Weinberg E L, Williamson O D; Canadian Pain Society. Pharmacological management of chronic neuropathic pain: revised consensus statement from the Canadian Pain Society. *Pain Res Manag.* 2014 November-December; 19(6):328-35. PMID: 25479151

Nakamura Y, Iga K, Shibata T, Shudo M, Kataoka K. Glial plasmalemmal vesicles: a subcellular fraction from rat hippocampal homogenate distinct from synaptosomes. *Glia.* 1993 September; 9(1):48-56. PMID: 7902337

Paluzzi S, Alloisio S, Zappettini S, Milanese M, Raiteri L, Nobile M, Bonanno G. Adult astroglia is competent for Na+/Ca2+ exchanger-operated exocytotic glutamate release triggered by mild depolarization. *J Neurochem.* 2007 November; 103(3):1196-207. PMID: 17935604

Pinza M, Farina C, Cerri A, Pfeiffer U, Riccaboni M T, Banfi S, Biagetti R, Pozzi O, Magnani M, Dorigotti L. Synthesis and pharmacological activity of a series of dihydro-1H-pyrrolo[1,2-a]imidazole-2,5(3H,6H)-diones, a novel class of potent cognition enhancers. *J Med Chem.* 1993 Dec. 24; 36(26):4214-20. PMID: 8277504

Randall L O, Selito J J. A method for measurement of analgesic activity on inflamed tissue. *Arch Int Pharmacodyn Ther.* 1957 September 1; 111(4):409-19. PMID: 13471093

Smith B H, Torrance N, Bennett M I, Lee A J. Health and quality of life associated with chronic pain of predominantly neuropathic origin in the community. *Clin J Pain.* 2007 February; 23(2):143-9. PMID: 17237663

Springuel G R, Leyssens T. Innovative chiral resolution using enantiospecific co-crystallization in solution. *Cryst Growth Des.* 2012; 12 (7): 3374-3378. DOI: 10.1021/cg300307z.

Torchio L, Lombardi F, Visconti M, Doyle E. Determination of the polar drug dimiracetam in human plasma and serum by column-switching high-performance liquid chromatography. *J Chromatogr B Biomed Appl.* 1995 Apr. 7; 666(1): 169-77. PMID: 7655615 van Hecke O, Austin S K, Khan R A, Smith B H, Torrance N. Neuropathic pain in the general population: a systematic review of epidemiological studies. Pain. 2014 April; 155(4):654-62. Erratum in: *Pain.* 2014 September; 155 (9):1907. PMID: 24291734

Wang Y, Chen A. Crystallization-based separation of enantiomers, in Stereoselective Synthesis of Drugs and Natural Products, 2nd volume; Andrushko V, Andrushko N, Eds. Wiley-Interscience, New York (2013). ISBN: 978-1-118-03217-6

Zilliox L A. Neuropathic Pain. Continuum (Minneap Minn.). 2017 April; 23(2, Selected Topics in Outpatient Neurology):512-532. PMID: 28375916.

EXAMPLES

Examples of the present invention are purely for illustrative and non-limiting purposes. Samples of racemic dimiracetam, (R)-dimiracetam, and (S)-dimiracetam can be synthesized using commercially available starting materials, namely:

Preparation of R,S-dimiracetam as Described in U.S. Pat. No. 5,200,406

|  | Supplier | Purity |
|---|---|---|
| 2-Chloroacetamide | Sigma Aldrich | 98% |
| Benzylamine | Sigma Aldrich | 99% |
| Ethyl trans-4-oxo-2-butenoate | Clariant | 98.5% |
| Ethyl acetate | Sigma Aldrich | 99.8% |
| Sodium hydroxide | Sigma Aldrich | 98% |
| Toluene | Sigma Aldrich | 98% |
| Palladium on charcoal | Sigma Aldrich | 5% |
| Methanol | Sigma Aldrich | 98% |
| Ammonium hydroxide | Sigma Aldrich | 30% |
| n-Butanol | Sigma Aldrich | 99% |

Preparation of R,S-Dimiracetam as Described in WO 2012/013640

| Glycinamide hydrochloride | Sigma Aldrich | 98% |
|---|---|---|
| Ethyl trans-4-oxo-2-butenoate | Clariant | 98.5% |
| Palladium on charcoal | Sigma Aldrich | 5% |
| Ethyl acetate | Sigma Aldrich | 99.8% |
| Sodium carbonate | Sigma Aldrich | 99.5% |
| Isopropanol | Sigma Aldrich | 99.7% |

Preparation of R-Dimiracetam as Described in WO 93/09120

| R-pyroglutamic acid | Sichuan Tongsheng Amino Acid Co. | 98% |
|---|---|---|
| Methanol | Sigma Aldrich | 98% |
| Methanesulfonic acid | Sigma Aldrich | 99% |
| Triethylamine | Sigma Aldrich | 99% |
| Ethyl acetate | Sigma Aldrich | 99.8% |
| Toluene | Sigma Aldrich | 98% |
| Sodium hydryde in oil | Sigma Aldrich | 60% |
| t-Butyl bromoacetate | Yancheng Longshen Chemical Co | 98.5% |
| Acetic acid | Sigma Aldrich | 99% |
| Ammonium hydroxide | Sigma Aldrich | 30% |
| Acetic anhydride | Sigma Aldrich | 98% |
| Sodium acetate | Sigma Aldrich | 99% |
| Dicloromethane | Sigma Aldrich | 98% |
| Sodium hydrogen carbonate | Sigma Aldrich | 99% |
| Isopropanol | Sigma Aldrich | 99% |
| Hydrochloric acid | Sigma Aldrich | 32% |

Preparation of S-Dimiracetam as Described in WO 93/09120

| S-pyroglutamic acid | Sigma Aldrich | 98% |
|---|---|---|
| Methanol | Sigma Aldrich | 98% |
| Methanesulfonic acid | Sigma Aldrich | 99% |
| Triethylamine | Sigma Aldrich | 99% |
| Ethyl acetate | Sigma Aldrich | 99.8% |
| Toluene | Sigma Aldrich | 98% |
| Sodium hydryde in oil | Sigma Aldrich | 60% |
| t-Butyl bromoacetate | Yancheng Longshen Chemical Co | 98.5% |

| | | |
|---|---|---|
| Acetic acid | Sigma Aldrich | 99% |
| Ammonium hydroxide | Sigma Aldrich | 30% |
| Acetic anhydride | Sigma Aldrich | 98% |
| Sodium acetate | Sigma Aldrich | 99% |
| Dicloromethane | Sigma Aldrich | 98% |
| Sodium hydrogen carbonate | Sigma Aldrich | 99.7% |
| Isopropanol | Sigma Aldrich | 99.7% |
| Hydrochloric acid | Sigma Aldrich | 32% |

These commercial supplies can be used as received from the supplier without further purification, using methods and techniques of preparative synthesis well known to those skilled in the art.

Example 1: Synthesis of the Composition of Dimiracetam (R)- and (S)-dimiracetam as well as the racemic mixture of dimiracetam were prepared in accordance with methods described in WO 93/09120; Pinza et al., 1993; and WO 2012/013640 as well as in Camilleri et al., 1993. The enantiomeric excess of the synthesized (R)- and (S)-dimiracetam was determined as described in Camilleri et al., 1993. The enantiomeric excess of (R)- and (S)-dimiracetam, when used separately for preparing the composition of the present invention, was equal to or greater than 96% for each enantiomer.

For achieving the desired enantiomeric excess of equal to or higher than 30% ee (excess (R)) and less than or equal to 60% ee (excess (R)), as well as other desired specific compositions in accordance with the present invention, several methods known to the skilled person in the art can be applied. For example, said compositions were prepared either by mixing the individual enantiomers or by mixing the racemate of dimiracetam with the respective quantities of (R)-dimiracetam. Furthermore, starting from racemic dimiracetam, part or all of the (S)-enantiomer can be removed by preparative chiral column chromatography.

Example 2: Inhibition of NMDA+Glycine-Induced Glutamate Release from Rat Spinal Synaptosomes Neurotransmitter Release Experiments Rat spinal synaptosomes, free from glial contaminants, were prepared according to the method of Paluzzi S. et al., 2007, a modification of the method of Nakamura et al., 1993, as follows.

Sprague-Dawley rats aged between 90 to 130 days were used. Animals were housed at constant temperature (22±1° C.) and relative humidity (50%) under a regular light-dark schedule (lights 7.00 am-7.00 pm). Food and water were freely available.

Rats were sacrificed by decapitation and the whole spinal cord was rapidly removed and maintained at 4° C. Rat spinal cord was homogenized (90 rpm; 24 up-down strokes in 2 min) in 10 volumes (1 g tissue in 10 ml) of ice cold 0.32 M sucrose, buffered at pH 7.4 using a glass-teflon tissue grinder (clearance 0.25 mm). The homogenate was centrifuged (5 min, 1000 g at 4° C.) to remove nuclei and debris, and the supernatant was gently stratified at 0-4° C. on a discontinuous Percoll® (Sigma Aldrich, St Louis, Mo., USA) gradient (2, 6, 10 and 20% v/v in Tris-buffered sucrose) and centrifuged at 33,500 g for 5 min. The layer between 10 and 20% Percoll (i.e. the synaptosomal fraction) was collected and washed by centrifugation in physiological medium having the following composition (mM): NaCl, 140; KCl, 3; $MgSO_4$ 1.2; $NaH_2PO_4$, 1.2; $NaHCO_3$ 5; $CaCl_2$ 1.2; HEPES 10; glucose, 10; pH 7.4. Protein content was measured according to Bradford M M, 1976 using bovine serum albumin as a standard.

Synaptosomes (about 70 µg protein) were incubated at 37° C. for 15 min in 2.5 mL of 0.05 µM [$^3$H]-D-aspartate ([$^3$H]-D-Asp; Perkin Elmer Italia, Monza, Milano, Italy). Then, the suspension was diluted to 122.5 mL with physiological medium maintained at 37° C. and 5 mL aliquots of the synaptosomal suspension were layered on microporous filters placed at the bottom of a set of 24 parallel 25 mL superfusion chambers maintained at 37° C. (Superfusion system, Ugo Basile, Comerio, Varese, Italy). Superfusion was then started with physiological medium at a rate of 0.5 mL/min, and was continued for 46 min. Starting at t=37 min, nine consecutive 1-min filtrate samples were collected. NMDA (10 µM) and glycine (1 µM) were introduced at the end of the first sample collected and maintained until the end of the experiment.

The radioactivity contained in each filtrate sample was measured by scintillographic methods, using a Ultima Gold scintillation fluid (Perkin-Elmer Milan, Italy). Each whole 0.5 mL sample was counted for radioactivity by adding 3 mL of scintillation fluid.

Tritium content measured in each sample was expressed as fractional percent (i.e. percent content of each sample with respect to total [$^3$H] content at the onset of the respective collection period). Drug effects were evaluated by calculating the ratio between the effluxes in the seventh fraction collected (in which the maximum effect of NMDA was reached) and that of the first fraction (basal release, prior to application of NMDA+glycine). This ratio was compared to the same seventh- and first-fraction ratio obtained under control conditions.

Effects on NMDA-Induced Glutamate Release in Synaptosomal Fractions

The possible effects of racemic and non-racemic dimiracetam mixtures on NMDA plus glycine-induced neurotransmitter release from rat spinal cord synaptosomes were assessed.

Figure 1B:
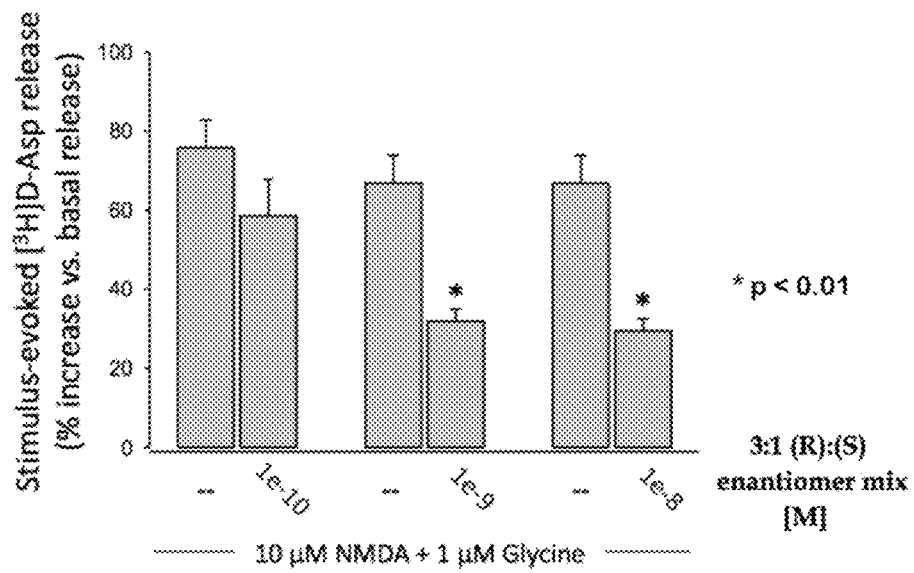
FIG. 1B: Effects of increasing molar concentrations of the inventive composition with an enantiomeric excess of (R)-dimiracetam of 50% (corresponding to a 3:1 (R):(S) ratio of the enantiomers) on NMDA (10 μM) plus glycine- (1 μM) stimulated release of [$^3$H]-D-Asp from pre-loaded spinal cord synaptosomes.
Figure 1C:
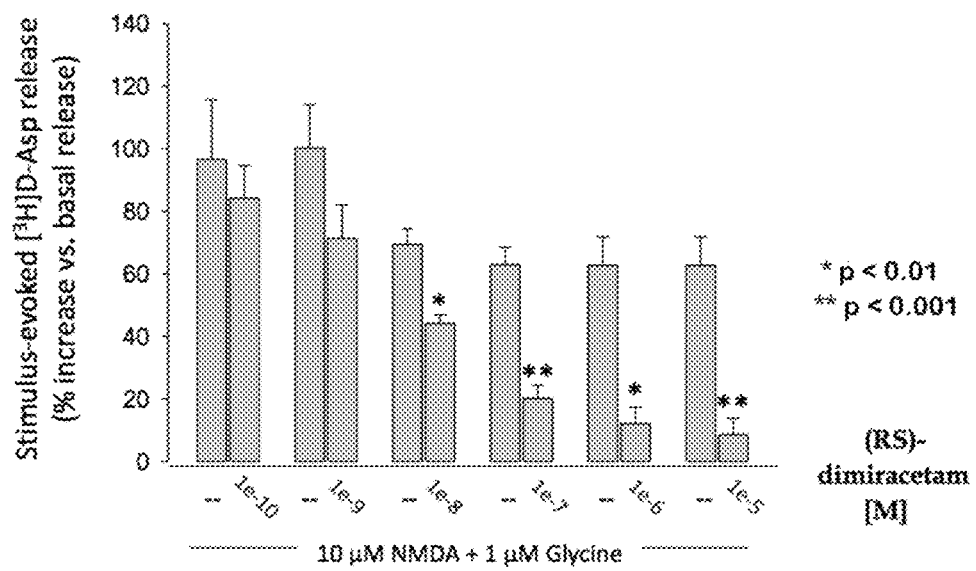
FIG. 1C: Effects of increasing molar concentrations of dimiracetam racemate on NMDA (10 μM) plus glycine- (1 μM) stimulated release of [$^3$H]-D-Asp from pre-loaded spinal cord synaptosomes.
Figure 1D:
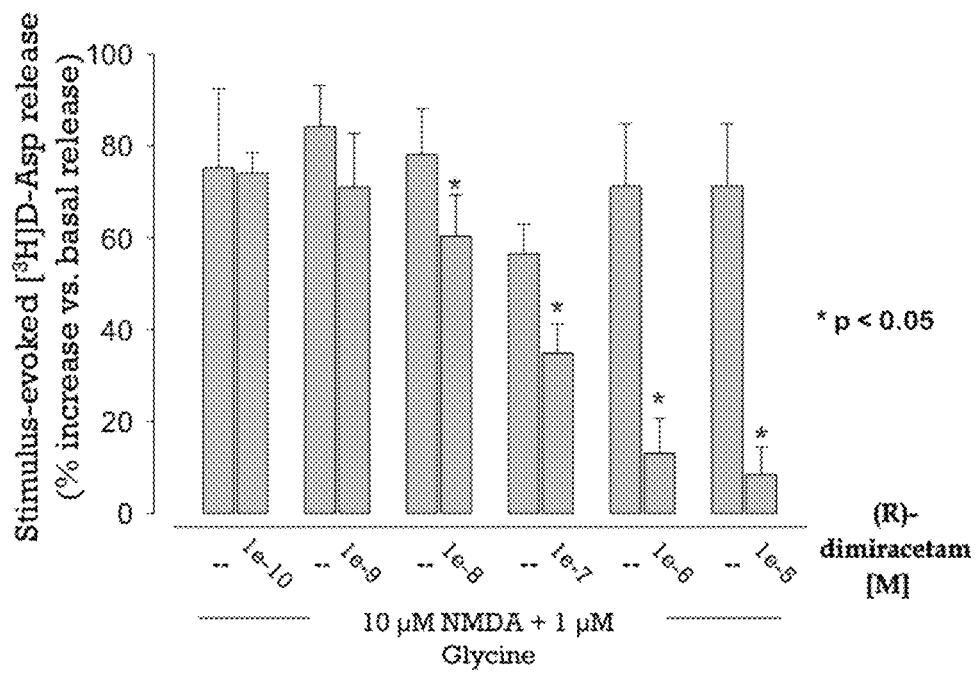
FIG. 1D: Effects of increasing molar concentrations of (R)-dimiracetam on NMDA (10 μM) plus glycine- (1 μM) stimulated release of [$^3$H]-D-Asp from pre-loaded spinal cord synaptosomes.
Figure 1E:
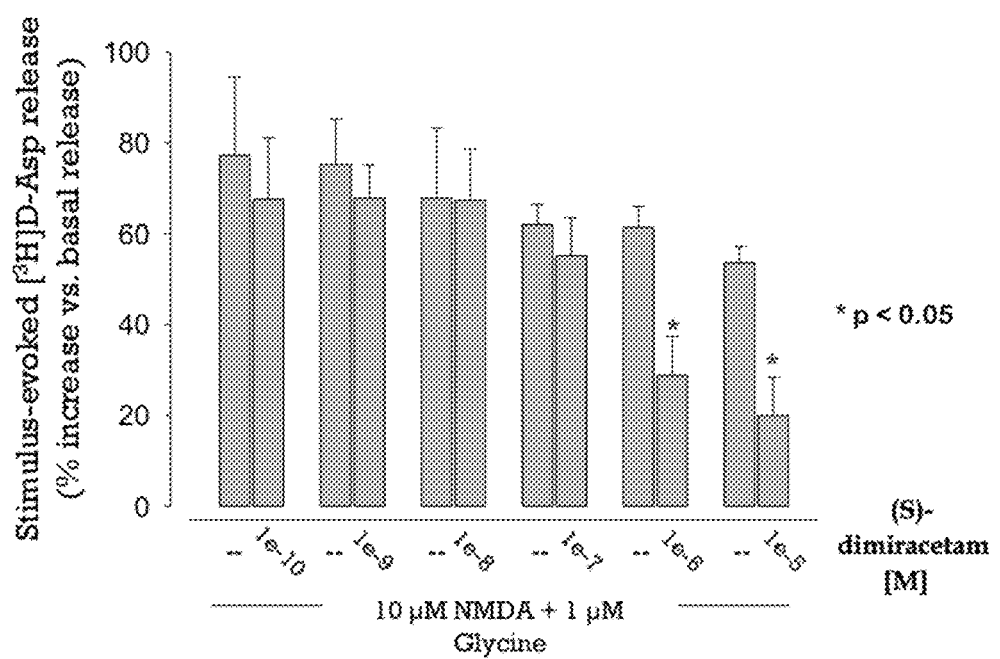
FIG. 1E: Effects of increasing molar concentrations of (S)-dimiracetam on NMDA (10 μM) plus glycine- (1 μM) stimulated release of [$^3$H]-D-Asp from pre-loaded spinal cord synaptosomes.

The inventive composition with an enantiomeric excess of (R)-dimiracetam of 33.3% corresponding to a 2:1 (R):(S) ratio of the dimiracetam enantiomers inhibits NMDA plus glycine-evoked [$^3$H]-D-aspartic acid release from rat spinal synaptosomes with an estimated $IC_{50}$ of 10 nM (FIG. 1A), wherein the inventive composition with an enantiomeric excess of (R)-dimiracetam of 50% corresponding to a 3:1 (R):(S) ratio of the dimiracetam enantiomers inhibits NMDA plus glycine-evoked [$^3$H]-D-aspartic acid release from rat spinal synaptosomes with an estimated $IC_{50}$ of less than 1 nM (FIG. 1B). In comparison, the racemic dimiracetam, i.e. 1:1 (R):(S), inhibits NMDA plus glycine-evoked [$^3$H]-D-aspartic acid release from rat spinal synaptosomes with an estimated $IC_{50}$ of 14.6 nM (FIG. 1C; Table 1), whereas the (R)-dimiracetam has an estimated $IC_{50}$ of 123 nM (FIG. 1D) and the (S)-dimiracetam an estimated $IC_{50}$ of 418 nM (FIG. 1E).

A further set of confirming experimental data is represented in Table 1.

TABLE 1

Inhibition by racemic dimiracetam and preferred inventive non-racemic dimiracetam mixtures on [$^3$H]-D-Asp release induced by 10 µM NMDA plus 1 µM glycine, in synaptosomes from rat spinal cord. Results are expressed as % inhibition of NMDA plus glycine-stimulated release. Data are means ± S.E.M. of 3 to 6 experiments that run in triplicate.

| Dimiracetam enantiomeric mixtures | | Percent inhibition of NMDA + glycine-induced glutamate release from rat spinal synaptosomes | | |
|---|---|---|---|---|
| (R):(S) ratio | Enantiomeric excess of (R)-dimiracetam | 0.1 nM | 1 nM | 10 nM |
| 1:1 | 0% | 9 ± 13% | 29 ± 3% | 35 ± 4% |
| 2:1 | 33% | 2 ± 17% | −3 ± 11% | 49 ± 7% |
| 3:1 | 50% | 21 ± 17% | 49 ± 10% | 54 ± 5% |

Example 3: Rat Models of Induced Peripheral Neuropathic Pain

Evaluation of Pain Responses

At the peak of the pain response according to the model under evaluation, the effects of a single dose of the test compounds, vehicles and comparators were evaluated. Thereafter, to assess the possible development of tolerance, repeated administrations of racemic and non-racemic dimiracetam mixtures were studied. Both hyperalgesia and allodynia were assessed. All efficacy evaluations were carried out by investigators blinded to the rats' treatment allocation.

Paw Pressure Test (Hyperalgesia)

Paw mechanical sensitivity was determined using a Randall & Selitto apparatus (Randall and Selitto, 1957) exerting a force that increases at constant rate (32 g/s). The stimulus causing paw withdrawal was evaluated before and at different times after treatment. Results represent the mean of mechanical thresholds for paw withdrawal expressed as grams. To avoid possible damage to the rat paw the maximum applied force was set at 240 g. In the single administration protocol, paw pressure tests were performed before (pre-dose) and at regular intervals after treatment.

Knee Osteoarthritis Model

A single intra-articular injection of sodium monoiodoacetate (MIA) was introduced into the knee joint of rats according to the method described by Fernihough J et al., 2004. Sodium monoiodoacetate (MIA) inhibits chondrocyte metabolism leading to cartilage degradation in form of osteoarthritic-like focal lesions in the cartilage associated with subchondral bone thickening 14 days after administration (Guingamp et al., 1997). This model therefore can easily and quickly reproduce osteoarthritic-like lesions and functional impairment in rats, similar to that observed in human disease (Guzman et al., 2003). After 7 days post-injection, the inflammatory component subsides and the remaining pain is considered neuropathic in nature. Briefly, rats were deeply anaesthetized with diethyl ether. Following abolition of the hind paw pinch withdrawal reflex, a 27-gauge needle was introduced into the joint cavity between the tibial plateau and femoral condyles. Once in place, 2 mg of MIA were diluted in a volume of 25 mL of 1% CMC (carboxymethylcellulose in water, Sigma-Aldrich, Italy) and injected into one knee joint and the rat was allowed to recover for 14 days prior to pain assessment.

Animals received a single administration of racemic dimiracetam (150 and 300 mg/kg p.o.) or compositions of (R) and (S) enantiomers of dimiracetam at 150 and 300 mg/kg in a ratio of 3:1 (R):(S) and 1:3 (R):(S) at day 16 after MIA injection. Control rats were treated with an equal volume of saline.

Chemotherapy Induced Peripheral Sensory Neuropathy—Oxaliplatin Model

Peripheral sensory neuropathy was induced in adult rats, by administration of oxaliplatin (Tocris) at 2.4 mg/kg i.p. in saline once daily for 5 consecutive days every week for three weeks (cumulative dose 36 mg/kg) according to Cavaletti et al., 2001. Starting from day 21 after the first oxaliplatin administration, the effect of repeated oral administration of racemic dimiracetam or the preferred inventive composition with an enantiomeric excess of (R)-dimiracetam of 50% corresponding to a 3:1 (R):(S) ratio of the enantiomers on oxaliplatin-induced mechanical hyperalgesia was assessed.

Example 4: Results of Experiments in Rat Models of Peripheral Neuropathic Pain

1. Knee Osteoarthritis Model

Influence of racemic dimiracetam and various compositions of non-racemic mixtures of dimiracetam enantiomers on peripheral neuropathic pain was assessed by paw-pressure test after a single intra-articular injection of sodium monoiodoacetate (MIA) into rat knee joint (knee osteoarthritis model) as described above.

Figure 2:
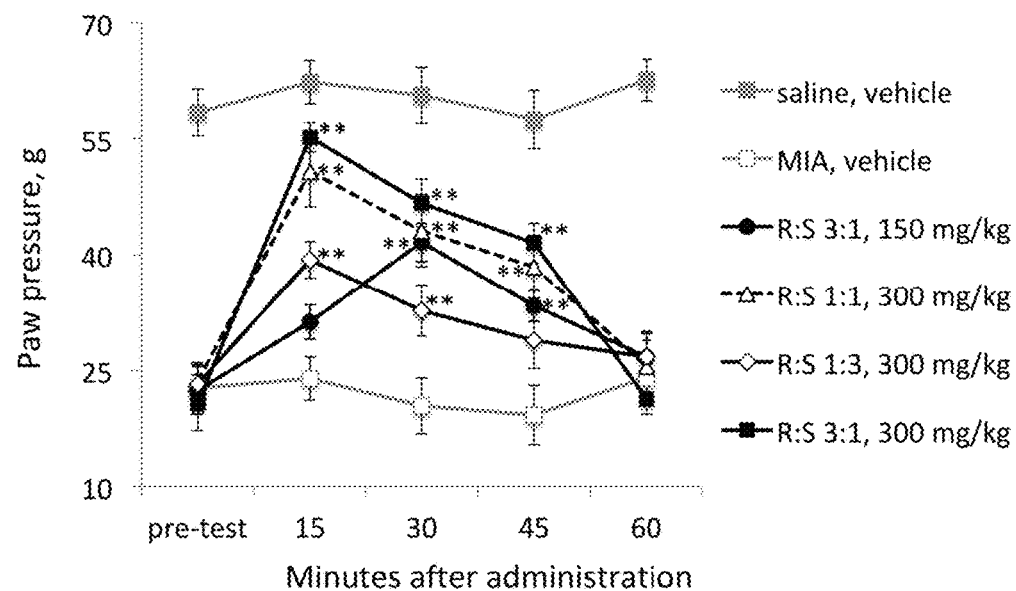
FIG. 2: Antihyperalgesic effect of a single dose of the inventive composition with an enantiomeric excess of (R)-dimiracetam of 50% (corresponding to a 3:1 (R):(S) ratio of the enantiomers) in comparison with dimiracetam racemate and a composition with an excess of the (S)-enantiomer of dimiracetam of 1:3 (R):(S) in a model of MIA-induced osteoarthritis in rats. Pain threshold was assessed by a Randall & Selitto analgesymeter. Results are expressed as grams and each value represents the mean±S.E.M. of 20 rats. **: P<0.01 versus vehicle-MIA.

FIG. 2 shows the results obtained in the paw-pressure test after single-dose oral administration of the racemic mixture of dimiracetam and different non-racemic mixtures of (R)-dimiracetam and (S)-dimiracetam, namely the preferred inventive composition with an enantiomeric excess of (R)-dimiracetam of 50% corresponding to a 3:1 (R):(S) ratio of the enantiomers, and a composition of 1:3 (R):(S). The preferred inventive composition with an enantiomeric excess of (R)-dimiracetam of 50% is more efficient in reducing peripheral neuropathic pain in the paw-pressure test after injection of sodium monoiodoacetate (MIA) than the racemic mixture of dimiracetam or a mixture with an excess of the (S)-enantiomer of dimiracetam [1:3 (R):(S)].

2. Oxaliplatin Model

After repeated oral administration of either racemic dimiracetam or the preferred inventive composition with an enantiomeric excess of (R)-dimiracetam of 50%, oxaliplatin-induced mechanical hyperalgesia was measured. Pain threshold was assessed by a Randall & Selitto analgesymeter before the morning administration. The preferred inventive composition with an enantiomeric excess of (R)-dimiracetam of 50% is more potent than racemic dimiracetam in reducing oxaliplatin-induced hyperalgesia (FIG. 3A), allodynia (FIG. 3B), and cold-sensitivity (FIG. 3C). Thus, also in this model of chemotherapeutically-induced peripheral sensory neuropathy, the inventive composition with an excess of the (R)-enantiomer of dimiracetam is more efficient in reducing peripheral neuropathic pain than the same amount of the racemic mixture of dimiracetam. Development of tolerance was not observed.

Figure 5:
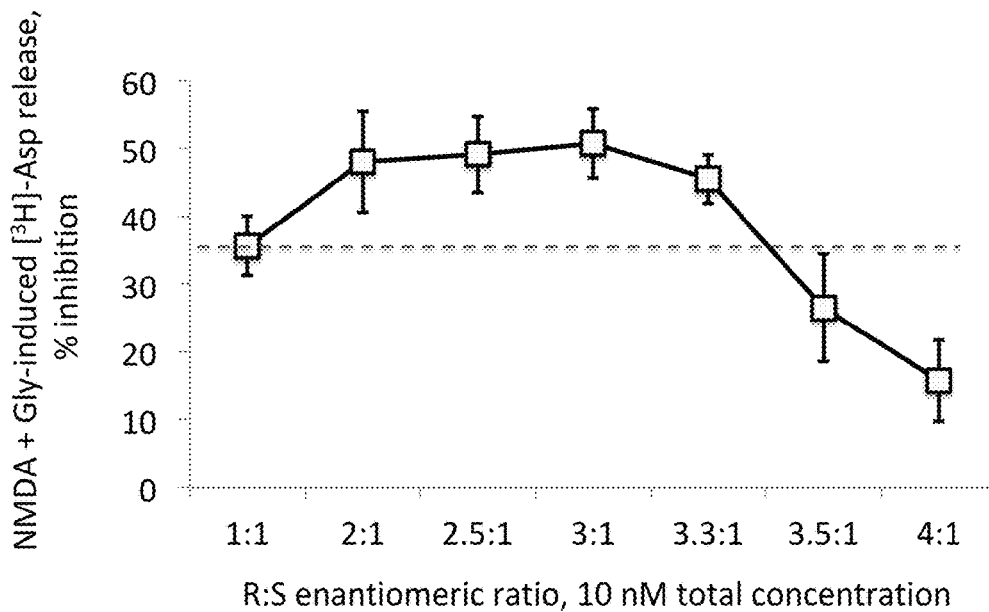
FIG. 5: Inhibition of NMDA+glycine-induced [3H]-D-aspartate release (square) by racemic dimiracetam (circle) and five different enantiomeric mixtures (circles with an R to S ratio from 2:1 to 4:1). This data was obtained in Example 5.

Example 5: In Vitro Inhibition of Pre-Loaded [3H]-D-Aspartate Release Induced by Added NMDA+Glycine in Rat Spinal Cord Synaptosomes In order to establish the range of (R):(S) ratios of enantiomeric mixtures of dimiracetam enantiomers providing an inhibitory potency superior to that of racemic dimiracetam, a number of mixtures between 2:1 to 4:1 (R):(S) were tested at 10 nM. These experiments were performed following the previously published methodology (Fariello et al. *Neuropharmacology.* 2014, (81), 85-94) and the results are shown in FIG. 5.

Furthermore, the data can be summarized as shown in the following Table 2:

TABLE 2

| R:S ratio | % inhibition (mean) | number of measurements | s.d. | s.e. |
|---|---|---|---|---|
| 1:1 | 35.4 | 8 | 12.3 | 4.4 |
| 2:1 | 48.0 | 9 | 22.3 | 7.4 |
| 2.5:1 | 49.1 | 8 | 15.8 | 5.6 |
| 3:1 | 50.7 | 9 | 15.3 | 5.1 |
| 3.3:1 | 45.5 | 8 | 10.1 | 3.6 |
| 3.5:1 | 26.5 | 10 | 25.3 | 8.0 |
| 4:1 | 15.7 | 10 | 18.9 | 6.0 | wherein s.d. is standard deviation and s.e. is the standard error of the mean.

As can be seen from this data, the compositions according to the present invention, in particular those having a ratio of 2:1 to 3.3:1 (R):(S), or in between said values, show a markedly improved inhibitory potency that is clearly superior to the inhibitory potency of racemic dimiracetam.

Example 6: In Vivo Anti-Amnestic Activity in a Passive Avoidance Paradigm in Mice Racemic dimiracetam and two different mixtures of its R and S enantiomers (2:1 (R):(S) and 3:1 (R):(S), respectively) were tested in a passive avoidance test in mice at doses of 3, 10 and 30 mg/kg, 30 min after oral administration.
Methods.

The test was performed according to the step-through method described by Jarvik M E ad Kopp R, *Psychol Rep,* 21:221-224, 1967. The apparatus consisted of a two-compartment acrylic box, with a lighted compartment connected to a darkened one by a guillotine door. Mice receive a punishing electrical shock (0.3 mA, 1 s) as soon as they entered the dark compartment. The test was performed on two consecutive days. Mice were placed in the light side of the two-compartment box: the latency times for entering the dark compartment were measured in the training session on the first day, and after 24 h in the retention session on the second day. Mice received the punishment when entering the dark room in the training session and remembered it in the session on the following day, unless their memory was impaired by the amnesic drug. In the training session, mice which had not entered the dark compartment after 60 s latency were excluded from the remainder of the experiment; about 20-30% of mice were excluded from each group. All investigated drugs were administered orally 30 min prior to the training session; for memory disruption, mice were injected with the amnesic drug scopolamine (1.5 mg/kg i.p.) immediately after completion of the training session.

Figure 6:
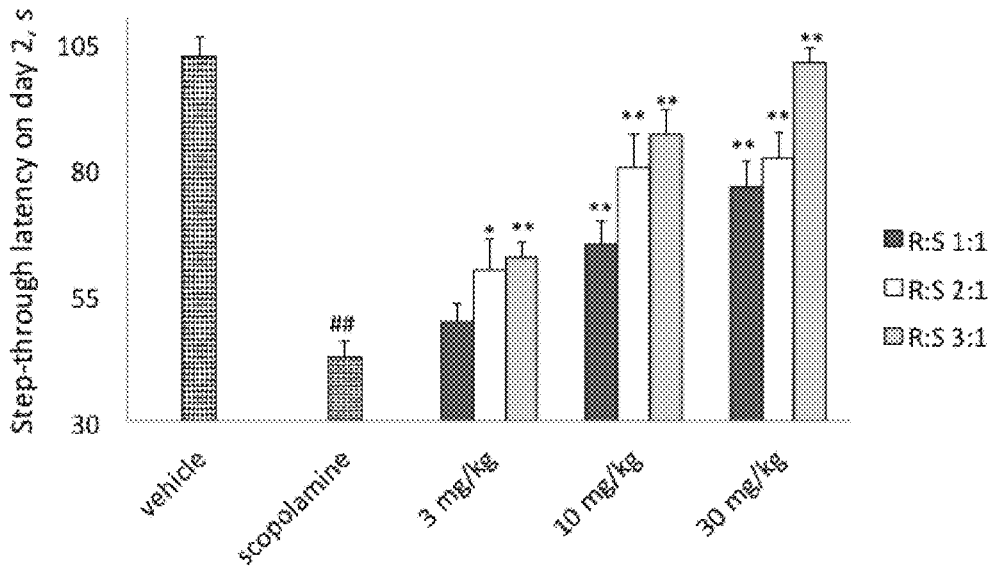
FIG. 6: Passive avoidance test. Enantiomeric mixtures of dimiracetam with three different R:S ratios (1:1, 2:1 and 3:1) were administered orally at 3, 10 or 30 mg/kg, 30 min before the training test on day 1. Scopolamine (1.5 mg/kg i.p.) was injected immediately after the punishment on day 1. The latency time recorded during the training session was comparable for all groups, (ca. 15 s). On day 2, the retention session was performed and the latency times are reported in bars. Data are expressed as mean±S.E.M. of 12 mice analyzed in 2 different experimental sets. ##P<0.01 vs vehicle+vehicle (vehicle); *P<0.05 and **P<0.01 vs scopolamine+vehicle (scopolamine).

Vehicle-treated mice received an i.p. injection of saline immediately after the training session, as control of the scopolamine injection. After 24 h, the test was repeated (retention session); during the second day no drug was administered. The maximum entry latency allowed in the retention session was 180 s. The results are shown in FIG. 6.

Accordingly, it can be seen that the latencies observed in the cases where a 3:1 ratio or a 2:1 ratio of R:S enantiomers was used, were much higher than in the case where the racemate of dimiracetam was used.

Example 7: Anti-Depressant Activity in the Forced Swimming (Porsolt) Test in Mice Racemic dimiracetam and two mixtures of its R and S enantiomers (2:1 and 3:1, respectively) were tested in forced swimming (Porsolt) test in mice at doses of 10, 30 and 100 mg/kg, 25 min after oral administration.
Methods.

Figure 7:
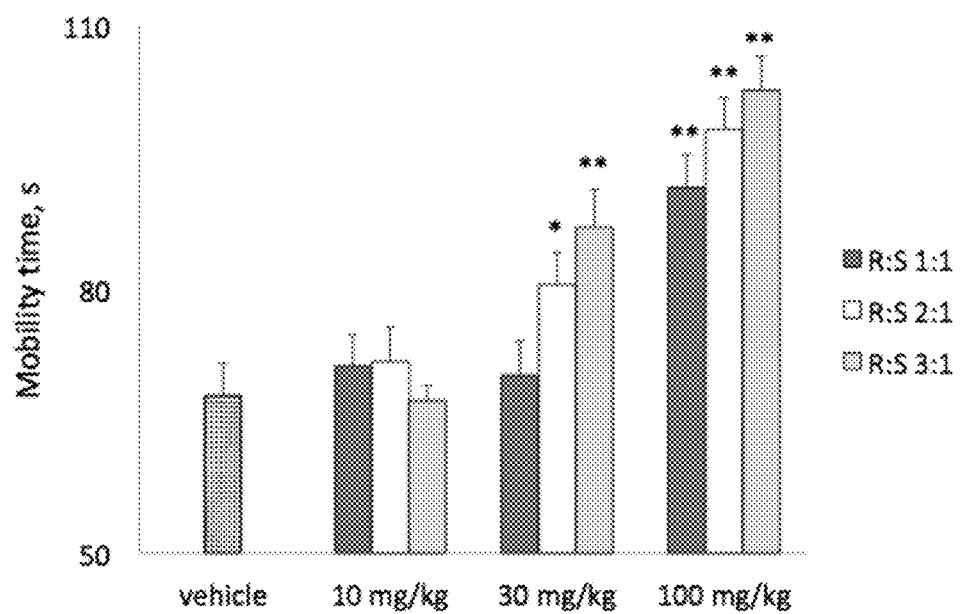
FIG. 7: Forced swimming test. Enantiomeric mixtures of dimiracetam with three different R:S ratios (1:1, 2:1 and 3:1) were administered orally at 10, 30 or 100 mg/kg, 25 min before the test. Mice were placed in water containing glass cylinders for 6 min, the duration of mobility was recorded during the last 4 min. Data are expressed as mean±S.E.M. of 12 mice analyzed in 2 different experimental sets. *P<0.05 and **P<0.01 vs vehicle+vehicle (vehicle) (indicting that animals were treated with vehicle instead of scopolamine and, subsequently, were again treated with vehicle instead of the test compound).

The forced swimming test used was the same as that described in Porsolt R D, Bertin A, Jalfre M, *Arch. Int Pharmacodyn. Ther.* 1977, 229:327-336. Briefly, mice were placed individually into glass cylinders (height: 25 cm, diameter: 10 cm) containing 12 cm of water maintained at 22-23° C. and were left there for 6 min. A mouse was judged to be immobile if it floated in the water, in an upright position, and made only small movements to keep its head above water. The duration of mobility was recorded during the last 4 min of the 6 min test. An increase in the duration of mobility was taken to be an indication of an antidepressant-like effect. The results are shown in FIG. 7.

Accordingly, it can be seen that the mobility of the mice that was achievable by the use of a 3:1 ratio or a 2:1 ratio of R:S enantiomers of dimiracetam was markedly higher that in the case of the racemate of dimiracetam.

In view of the above, it can be seen that the effects of the claimed ratios of R:S enantiomers of dimiracetam lead to reduced glutamate release from rat spinal synaptosomes, reduced peripheral neuropathic pain, anti-amnestic effects and anti-depressant effects that are clearly better than in the case where the racemate of dimiracetam was used.

Figure 3:
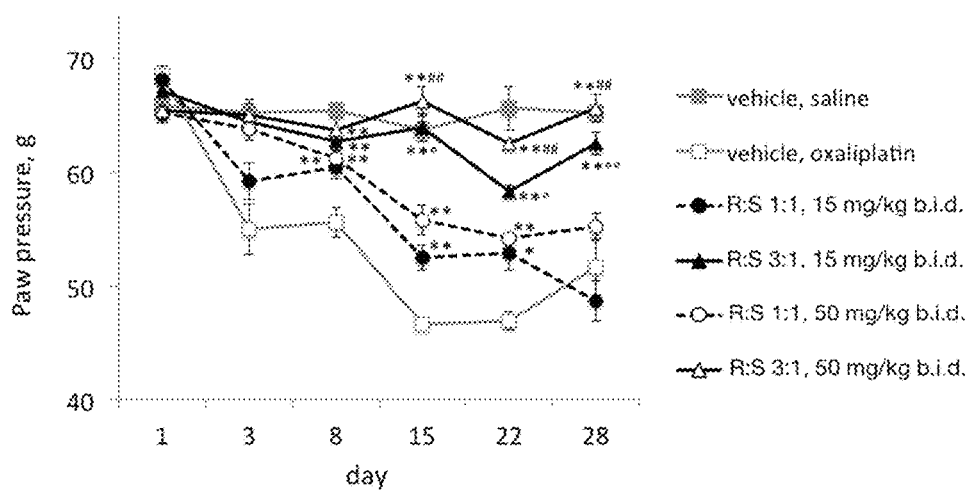
FIG. 3: Effect of repeated oral administration of the inventive composition with an enantiomeric excess of (R)-dimiracetam of 50% (corresponding to a 3:1 (R):(S) ratio of the enantiomers) and dimiracetam racemate on oxaliplatin-induced mechanical hyperalgesia. Pain threshold was assessed by a Randall & Selitto analgesymeter before the morning administration and each value represents the mean±S.E.M. of 6 rats. *P<0.05 and **P<0.01 and vs oxaliplatin+vehicle treated animals; ° P<0.05 and ° ° P<0.01 vs oxaliplatin+dimiracetam 15 mg/kg; #P<0.05 and ##P<0.01 vs oxaliplatin+dimiracetam 50 mg/kg.
Figure 4A:
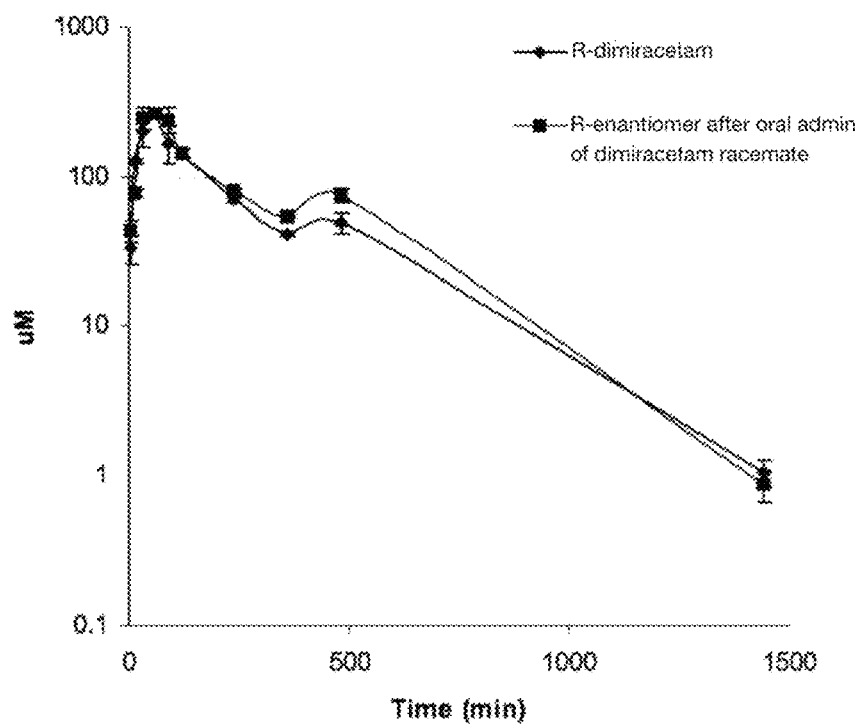
FIG. 4A: Comparison of the plasma concentration-time profiles of the (R)-enantiomer after oral administration of (R)-dimiracetam (75 mg/kg) and after oral administration of racemic dimiracetam (150 mg/kg)
Figure 4B:
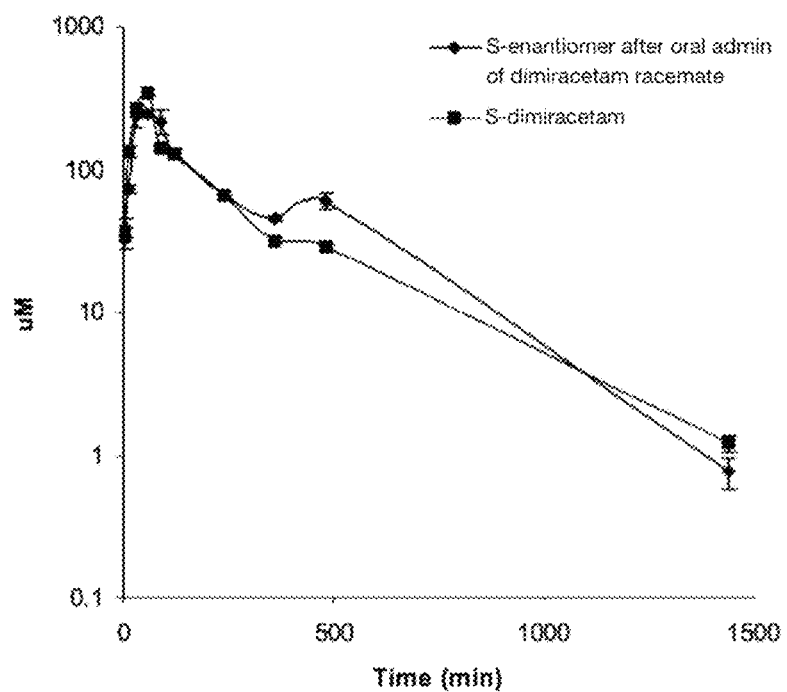
FIG. 4B: Comparison of the plasma concentration-time profiles of the (S)-enantiomer after oral administration of (S)-dimiracetam (2) (75 mg/kg) and after oral administration of racemic dimiracetam (150 mg/kg).

Example 8: Paw Pressure Test, Von Frey Test and Cold Plate Test in Oxaliplatin Model in Rats After repeated oral administration of either racemic dimiracetam or the preferred inventive composition with an enantiomeric excess of (R)-dimiracetam of 50%, oxaliplatin-induced mechanical hyperalgesia was measured. Pain threshold was assessed by a Randall & Selitto analgesymeter (Leighton et al. *Br. J. Pharmacol.* 93:553-560, 1988) before the morning administration. In the morning of day 28, also mechanical allodynia (Sakurai et al. *Pain* 147:165-74, 2009) and cold sensitivity were assessed, using the von Frey and cold plate tests (Di Cesare Mannelli et al. *Exp Neurol* 261:22-33, 2014), respectively. As shown in FIG. 3 and Table 3, the preferred inventive composition with an enantiomeric excess of (R)-dimiracetam of 50% is more potent in reducing oxaliplatin-induced hyperalgesia, allodynia and cold sensitivity. Thus, also in this model of chemotherapeutically induced peripheral sensory neuropathy, the inventive composition with an excess of the (R)-enantiomer of dimiracetam is more efficient in reducing peripheral neuropathic pain than the racemic mixture of dimiracetam. Development of tolerance was not observed.

TABLE 3

Effect of racemic dimiracetam and invention mixture (R:S 3:1)

| Treatment Dose mg/kg b.i.d. | Randall & Selitto, paw pressure, g Pre-test | Day 28 | Von Frey paw, withdrawal, g Pre-test | Day 28 | Cold plate, licking latency, s Pre-test | Day 28 |
|---|---|---|---|---|---|---|
| saline | 65.8 ± 1.8 | 65.2 ± 0.9 | 23.0 ± 0.8 | 26.3 ± 0.8 | 22.5 ± 0.9 | 20.5 ± 0.7 |
| oxaliplatin | 68.5 ± 1.1 | 51.7 ± 1.9 | 20.6 ± 0.9 | 15.9 ± 1.0 | 23.5 ± 0.6 | 14.2 ± 0.6 |
| R:S 1:1 15 | 68.1 ± 1.2 | 48.7 ± 2.5 | 21.4 ± 1.0 | 16.0 ± 1.5 | 21.5 ± 1.0 | 14.8 ± 1.5 |
| R:S 3:1 15 | 65.2 ± 1.7 | 62.5 ± 1.8**°° | 25.1 ± 0.5 | 24.7 ± 1.5**°° | 20.8 ± 1.3 | 18.7 ± 0.7**°° |
| R:S 1:1 50 | 67.1 ± 0.8 | 55.2 ± 1.0 | 21.4 ± 0.5 | 18.5 ± 2.3 | 22.0 ± 0.8 | 15.4 ± 1.0 |
| R:S 3:1 50 | 65.4 ± 1.2 | 65.6 ± 1.2**## | 21.2 ± 1.1 | 22.1 ± 0.8**° | 21.9 ± 2.1 | 19.6 ± 0.7**## |

Oxaliplatin (2.4 mg/kg i.p.) was administered daily on weekdays from day 1 to day 15 (11 injections in total). The two mixtures of dimiracetam enantiomers (R:S 1:1 and R:S 3:1) were administered daily from day 1 until day 27. Behavioral measurements were performed in the morning of day 28 and represent the mean ± s.e.m of 6 rats.
$P < 0.01$ vs saline;
**$P < 0.01$ vs oxaliplatin;
°$P < 0.05$ and °°$P < 0.01$ vs racemate 15 mg/kg;
$P < 0.05$ and ##$P < 0.01$ vs racemate 50 mg/kg The paw pressure test, Von Frey test and cold plate test were conducted as follows:

Paw Pressure Test

Paw mechanical sensitivity was determined using a Randall & Selitto apparatus exerting a force that increases at constant rate (32 g/s). The stimulus at which rats withdrew the paw was evaluated before and at different times after treatment. Results represent the mean of mechanical thresholds expressed as grams. To avoid any possible damage to the animal paw the maximum applied force was fixed at 240 g (Leighton et al. Br. J. Pharmacol. 93:553-560, 1988).

Von Frey Test

The animals were placed in 20 cm×20 cm Plexiglas boxes equipped with a metallic mesh floor, 20 cm above the bench. Animals were allowed to habituate themselves to their environment for 15 min before the test. An electronic Von Frey hair unit (Ugo Basile, Varese, Italy) was used: the withdrawal threshold was evaluated by applying forces ranging from 0 to 50 g with a 0.2 g accuracy. Punctuate stimulus was delivered to the mid-plantar area of each anterior paw from below the mesh floor through a plastic tip and the withdrawal threshold was automatically displayed on the screen. The paw sensitivity threshold was defined as the minimum force required to elicit a robust and immediate withdrawal reflex of the paw. Voluntary movements associated with locomotion were not considered as a withdrawal response. Stimuli were applied to each posterior paw at 5 s intervals. Measurements were repeated 5 times and the final value was obtained by averaging the 5 measurements (Sakurai et al. Pain 147:165-74, 2009).

Cold Plate Test

The animals were placed in a stainless box (12 cm×20 cm×10 cm) with a cold plate as floor. The temperature of the cold plate was kept constant at 4° C.±1° C. Pain-related behaviors (i.e. lifting and licking of the hind paw) were observed and the time (s) of the first sign was recorded. The cut-off time of the latency of paw lifting or licking was set at 60 s (Di Cesare Mannelli et al. Exp Neurol 261:22-33, 2014).

All patents, publications, and abstracts cited above are incorporated herein by reference in their entireties. Various embodiments of the invention have been described in fulfillment of the various objectives of the invention. It should be recognized that these embodiments are merely illustrative of the principles of the present invention. Numerous modifications and adaptions thereof will be readily apparent to those skilled in the art without departing from the spirit and scope of the present invention as defined in the following claims.

What is claimed is:

1. A composition comprising (R)-3,6,7,7a-tetrahydro-1H-pyrrolo[1,5-a]imidazole-2,5-dione ((R)-dimiracetam (1)) and (S)-3,6,7,7a-tetrahydro-1H-pyrrolo[1,5-a]imidazole-2,5-dione ((S)-dimiracetam (2)),

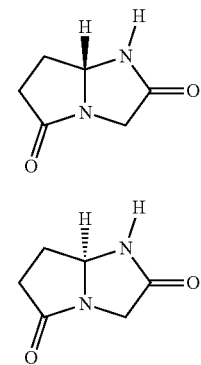

and/or pharmaceutically acceptable solvates or co-crystals thereof,
wherein an enantiomeric excess (ee) of the (R)-dimiracetam (1) is equal to or higher than 33% and lower than or equal to 54%.

2. The composition of claim 1, wherein a ratio of (R)-dimiracetam (1) to (S)-dimiracetam (2) is 2:1 to 3.3:1.

3. The composition of claim 1, wherein the
(R)-dimiracetam (1) and/or pharmaceutically acceptable solvates or co-crystals thereof and
(S)-dimiracetam (2) and/or pharmaceutically acceptable solvates or co-crystals thereof are packaged separately.

4. The composition of claim 1, wherein the composition is a non-racemic mixture of 3,6,7,7a-tetrahydro-1H-pyrrolo[1,5-a]imidazole-2,5-dione (dimiracetam) and pharmaceutically acceptable solvates or co-crystals thereof, wherein the non-racemic mixture comprises (R)-dimiracetam (1) to (S)-dimiracetam (2) in an enantiomeric excess (ee) of the (R)-dimiracetam (1) of equal to or higher than 33% and lower than or equal to 54%.

5. A pharmaceutical composition comprising the composition of claim 1 and a pharmaceutically acceptable carrier.

6. A method at treating a disease, injury, or disorder, comprising: administering to a subject the composition of claim 1, wherein the disease, injury, or disorder is peripheral sensory neuropathy, seizure, depression, or cognitive impairment.

7. The method of claim 6, wherein the disease, injury, or disorder is peripheral sensory neuropathy, a neuropsychiatric disorder, a motoneuron disorder, or a movement disorder.

8. The method of claim 6, wherein the disease, injury, or disorder is peripheral sensory neuropathy.

9. The method of claim 8, wherein the peripheral sensory neuropathy is peripheral neuropathic pain.

10. The method of claim 8, wherein the peripheral sensory neuropathy is diabetic neuropathy, post-herpetic neuropathy, lumbago, sacral pain, surgical pain, crush injury, spinal injury, complex regional pain syndrome, phantom limb sensations, peripheral sensory neuropathy associated with osteoarthritis, peripheral sensory neuropathy associated with rheumatoid arthritis, peripheral sensory neuropathy associated with autoimmune osteoarthrosis, cephalea, fibromyalgia, peripheral sensory neuropathy induced by antiblastic therapies, peripheral sensory neuropathy induced by a chemotherapeutic agent, peripheral sensory neuropathy associated with visceral injury, peripheral sensory neuropathy associated with osteonecrosis, peripheral sensory neuropathy associated with human immunodeficiency virus infection, peripheral neuropathic pain, or peripheral sensory neuropathy induced by an antiviral agent.

11. The method of claim 8, wherein the peripheral sensory neuropathy is peripheral sensory neuropathy induced by a chemotherapeutic agent or peripheral sensory neuropathy induced by an antiviral agent.

12. The method of claim 11, wherein the peripheral sensory neuropathy is peripheral sensory neuropathy induced by a chemotherapeutic agent, wherein the chemotherapeutic agent is selected from the group consisting of a kinase inhibitor, a proteasome inhibitor, a taxane, a vinca alkaloid, and a platinum salt, and wherein preferably the chemotherapeutic agent is selected from sorafenib, sunitinib, afatinib, axitinib, vandetanib, vemurafenib, ixazomib, bortezomib, paclitaxel, docetaxel, cabazitaxel, vincristine, vinblastine, vindesine, vinorelbine, nedaplatin, lobaplatin, picoplatin, satraplain, cisplatin, carboplatin, and oxaliplatin.

13. The method of claim 11, wherein the peripheral sensory neuropathy is peripheral sensory neuropathy induced by an antiviral agent, wherein the antiviral agent is a nucleoside reverse transcriptase inhibitor.

14. The method of claim 13, wherein the nucleoside reverse transcriptase inhibitor is zalcitabine, didanosine, stavudine, or zidovudine.

15. The method of claim 6, further comprising administering an antitumor drug, wherein the antitumor drug is selected from the group consisting of a kinase inhibitor, a proteasome inhibitor, a taxane, a vinca alkaloid, and a platinum salt.

16. The method of claim 15, wherein the antitumor drug is selected from the group consisting of sorafenib, sunitinib, afatinib, axitinib, vandetanib, vemurafenib, ixazomib, bortezomib, paclitaxel, docetaxel, cabazitaxel, vincristine, vinblastine, vindesine, vinorelbine, nedaplatin, lobaplatin, picoplatin, satraplain, cisplatin, carboplatin, and oxaliplatin.

17. The method of claim 6, further comprising administering an antiviral drug, wherein the antiviral drug is a nucleoside or a nucleotide.

18. The method of claim 17, wherein the antiviral drug is of zalcitabine, didanosine, stavudine, or zidovudine.

19. The method of claim 6, wherein the composition is administered orally twice daily in a dose of between 10 mg and 3000 mg per administration, between 20 mg to 2000 mg per administration, or between 50 mg and 1000 mg per administration.

20. A method of enhancing learning and memory, comprising administering to a subject the composition of claim 1.

21. The method of claim 20, wherein the subject is a healthy subject.

22. A method for preparing a composition of claim 1, comprising combining
(R)-dimiracetam (1) and (S)-dimiracetam (2), or
(R)-dimiracetam (1) and a racemate of dimiracetam.

23. A kit of parts comprising (R)-dimiracetam (1) and (S)-dimiracetam (2) and instructions for combining (R)-dimiracetam (1) and (S)-dimiracetam (2) to obtain an enantiomeric excess (ee) of the (R)-dimiracetam (1) of equal to or higher than 33% and lower than or equal to 54%.

* * * * *